US010118942B2

(12) United States Patent
Morse et al.

(10) Patent No.: US 10,118,942 B2
(45) Date of Patent: Nov. 6, 2018

(54) TOLL-LIKE RECEPTOR 2 LIGANDS AND METHODS OF MAKING AND USING THEREOF

(71) Applicants: H. LEE MOFFITT CANCER CENTER AND RESEARCH INSTITUTE, INC., Tampa, FL (US); THE ARIZONA BOARD OF REGENTS ON BEHALF OF THE UNIVERSITY OF ARIZONA, Tucson, AZ (US); UNIVERSITY OF SOUTH FLORIDA, Tampa, FL (US)

(72) Inventors: David L. Morse, Tampa, FL (US); Josef Vagner, Tucson, AZ (US); Mark McLaughlin, Tampa, FL (US); Robert Gillies, Tampa, FL (US); Amanda Huynh, Land O Lakes, FL (US); Michael Doligalski, Lutz, FL (US)

(73) Assignees: H. Lee Moffitt Cancer Center and Research Institute, Inc., Tampa, FL (US); The Arizona Board of Regents on behalf of the University of Arizona, Tucson, AZ (US); University of South Florida, Tampa, FL (US)

( * ) Notice: Subject to any disclaimer, the term of this patent is extended or adjusted under 35 U.S.C. 154(b) by 0 days.

(21) Appl. No.: 15/561,230

(22) PCT Filed: Mar. 25, 2016

(86) PCT No.: PCT/US2016/024327
§ 371 (c)(1),
(2) Date: Sep. 25, 2017

(87) PCT Pub. No.: WO2016/154586
PCT Pub. Date: Sep. 29, 2016

(65) Prior Publication Data
US 2018/0051055 A1 Feb. 22, 2018

Related U.S. Application Data
(60) Provisional application No. 62/138,658, filed on Mar. 26, 2015.

(51) Int. Cl.
A61K 49/00 (2006.01)
C07K 5/083 (2006.01)
A61K 51/04 (2006.01)

(52) U.S. Cl.
CPC .......... *C07K 5/081* (2013.01); *A61K 49/0019* (2013.01); *A61K 49/0032* (2013.01); *A61K 49/0052* (2013.01); *A61K 51/0497* (2013.01)

(58) Field of Classification Search
CPC ............... A61K 49/00; A61K 2123/00; A61K 2121/00; A61K 49/0032; A61K 49/0052; A61K 51/00; A61K 51/0497; A61K 49/0019; C07K 5/081

USPC .... 424/1.11, 1.65, 1.81, 1.85, 1.89, 9.1, 9.2, 424/9.3, 9.4, 9.5, 9.6, 1.69; 514/1, 19.2, 514/19.3, 19.4, 19.5, 19.6
See application file for complete search history.

(56) References Cited

U.S. PATENT DOCUMENTS

| | | |
|---|---|---|
| 6,960,648 B2 | 11/2005 | Bonny |
| 8,580,255 B2 * | 11/2013 | Heffernan ........ C07K 14/70596 424/130.1 |
| 2002/0035243 A1 | 3/2002 | Imfeld et al. |
| 2002/0120100 A1 | 8/2002 | Bonny |
| 2003/0032594 A1 | 2/2003 | Bonny |
| 2014/0161725 A1 | 6/2014 | Morse et al. |

OTHER PUBLICATIONS

Agnihotri, et al., Structure-activity relationships in toll-like receptor 2-agonists leading to simplified monoacyl lipopeptides. J Med Chem 2011, 54(23):8148-60.
Cheng, et al., Discovery of small-molecule inhibitors of the TLR1/TLR2 complex. Angew Chem Int Ed Engl 2012, 51(49):12246-9.
Ferrone, et al., Pancreatic adenocarcinoma: the actual 5-year survivors. J Gastroinstest Surg 2008, 12(4):701-6.
Handl, et al., Development of a lanthanide-based assay for detection of receptor-ligand interactions at the delta-opioid receptor. Anal Biochem 2005, 343(2):299-307.
Handl, et al., Lanthanide-based time-resolved fluorescence of in cyto ligand-receptor interactions. Anal Biochem 2004, 330(2):242-50.
Howard, et al., A margin-negative R0 resection accomplished with minimal postoperative complications is the surgeon's contribution to long-term survival in pancreatic cancer. J Gastrointest Surg 2006, 10(10):1338-45.
Huynh, et al., Novel Toll-like Receptor 2 Ligands for Targeted Pancreatic Cancer Imaging and Immunotherapy. J Med Chem 2012, 55(22):10.102/jm301002f.
Huynh, et al., Tumor Targeting and Pharmacokinetics of a Near-Infrared Fluorescent-Labeled delta-Opioid Receptor Antagonist Agent, Dmt-Tic-Cy5. Mol Pharm 2016., 13(2):534-544.
Josan et al., Solid-phase synthetic strategy and bioevaluation of a labeled delta-opioid receptor ligand Dmt-Tic-Lys for in vivo imaging. Org Lett 2009, 11(12):2479-82.
(Continued)

*Primary Examiner* — D. L. Jones
(74) *Attorney, Agent, or Firm* — Meunier Carlin & Curfman LLC

(57) ABSTRACT

Disclosed are monoacylated Toll-like receptor 2 ligands which can be used in both the development of targeted agents for the imaging and treatment of pancreatic cancer as well as other cancers, and as an adjuvant for cancer immunotherapy. The monoacylated compounds disclosed herein have a higher binding affinity for TLR2 relative to a known potent diacylated agonists, but only ~½ the bioactivity. Competition of the monoacylated compound with the diacylated compound for binding TLR2 was confirmed. Hence, the reported monoacylated compounds are inhibitors/antagonists of TLR2 activation.

12 Claims, 5 Drawing Sheets

(56) References Cited

OTHER PUBLICATIONS

Josan, J. S.; De Silva, C. R.; Yoo, B.; Lynch, R. M.; Pagel, M. D.; Vagner, J.; Hruby, V. J., Fluorescent and lanthanide labeling for ligand screens, assays, and imaging. Methods Mol Biol 2011, 716, 89-126.

Keana, Newer Aspects of Synthesis and Chemistry of Nitroxide Spin Labels, Chem Rev 1978, 78(1):37-64.

Krchnak, et al., Color-monitored solid-phase multiple peptide synthesis under low-pressure continuous-flow conditions. Pept Res 1990, 3(4):182-93.

Krchnak et al., Noninvasive continuous monitoring of solid-phase peptide synthesis by acid-base indicator. Int J Pept Protein Res 1988, 32(5):415-6.

Metildi, et al., Ratiometric activatable cell-penetrating peptides label pancreatic cancer, enabling fluorescence-guided surgery, which reduces metastases and recurrence in orthotopic mouse models. Ann Surg Oncol 2015, 22(6):2082-7.

Mistry, et al., Inhibition of TLR2 signaling by small molecule inhibitors targeting a pocket within the TLR2 TIR domain. Proc Natl Acad Sci 2015, 112(17):5455-60.

Morse et al., Identification of novel pancreatic adenocarcinoma cell-surface targets by gene expression profiling and tissue microarray. Biochem Pharmacol 2010, 80(5):748-54.

Murgueitio, et al., Prospective virtual screening in a sparse data scenario: design of small-molecule TLR2 antagonists. Chem Med Chem 2014, 9(4):813-22.

Reid, et al., Authentication of Human Cell Lines by STR DNA Profiling Analysis. In Assay Guidance Manual, Sittampalam, G. S.; et al., Eds. Bethesda (MD), 2004.

Salunke, et al., Structure-activity relationships in human Toll-like receptor 2-specific monoacyl lipopeptides. J Med Chem 2012, 55(7):3353-63.

Schindler, et al., Three NF-kappa B binding sites in the human E-selectin gene required for maximal tumor necrosis factor alpha-induced expression. Mol Cell Biol 1994, 14(9):5820-31.

Seyberth, et al., Lipolanthionine peptides act as inhibitors of TLR2-mediated IL-8 secretion. Synthesis and structure-activity relationships. J Med Chem 2006, 49(5):1754-65.

Sturm, et al., Targeted imaging of esophageal neoplasia with a fluorescently labeled peptide: first-in-human results. Sci Transl Med 2013, 5(184), 19 pages.

Troyan, et al., The FLARE intraoperative near-infrared fluorescence imaging system: a first-in-human clinical trial in breast cancer sentinel lymph node mapping. Ann Surg Oncol 2009, 16(10):2943-52.

Vagner, et al., Heterobivalent ligands crosslink multiple cell-surface receptors: the human melanocortin-4 and delta-opioid receptors. Angew Chem Int Ed Engl 2008, 47(9):1685-8.

van Dam, et al., Intraoperative tumor-specific fluorescence imaging in ovarian cancer by folate receptor-alpha targeting: first in-human results. Nat Med 2011, 17(10):1315-9.

van der Vorst, et al., Near-infrared fluorescence-guided resection of colorectal liver metastases. Cancer 2013, 119(18):3411-8.

Zhong, et al., Structure-based discovery of an immunomodulatory inhibitor of TLR1-TLR2 heterodimerization from a natural product-like database. Chem Commun (Camb) 2015, 51(56):11178-81.

Zhou, et al., Discovery of a novel TLR2 signaling inhibitor with anti-viral activity. Antiviral Res 2010, 87(3):295-306.

International Search Report and Written Opinion issued for International Application No. PCT/US2016/024327, dated Jun. 20, 2016.

PUBCHEM, Substance Record for SID 163348474, Create date: May 31, 2013 [retrieved on May 9, 2016].

PUBCHEM, Substance Record for SID 163348479, Create date: May 31, 2013 [retrieved on May 9, 2016].

International Preliminary Report on Patentability issued for International Application No. PCT/US2016/024327, dated Oct. 5, 2017.

* cited by examiner

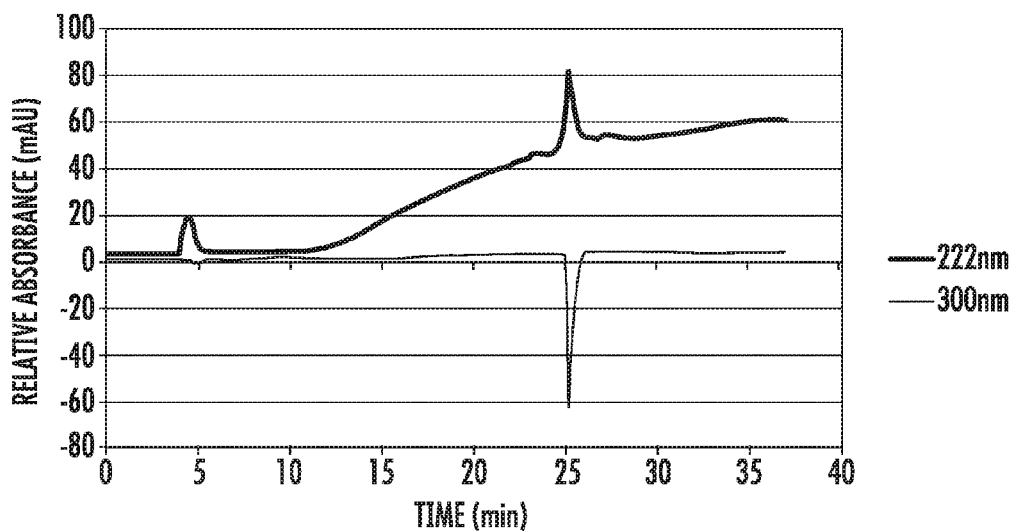
FIG. 1
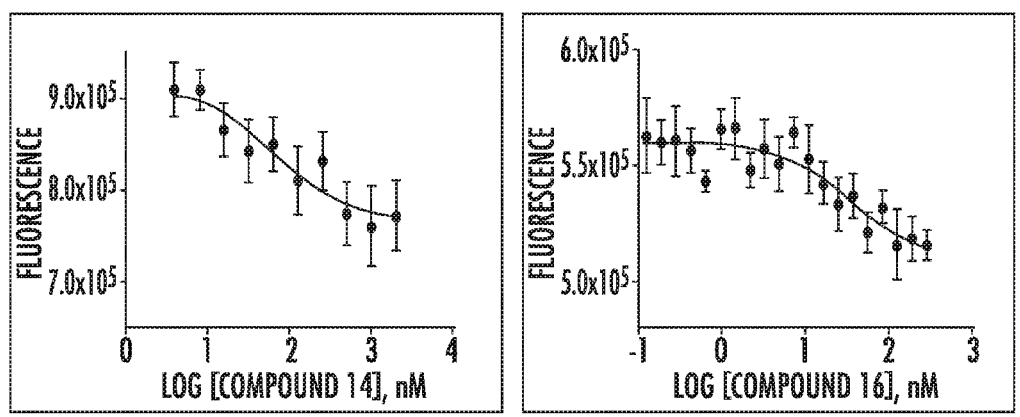
FIG. 2A
FIG. 2B

ULTRASOUND IN VIVO IMAGING

INTRAOPERATIVE DETECTION

EX VIVO FLUORESCENCE IMAGING

FMT IN VIVO IMAGING
PRE SURGERY    POST SURGERY

FL SURGERY GROUP 2:17-2

TOLL-LIKE RECEPTOR 2 LIGANDS AND METHODS OF MAKING AND USING THEREOF

This invention was made with government support under Grant No. R01 CA123547-03 awarded by the National Institutes of Health. The government has certain rights in the invention.

CROSS REFERENCE TO RELATED APPLICATION

Background

Toll-like Receptor 2 (TLR2) is a type I transmembrane glycoprotein characterized by an external antigen recognition domain comprised of a highly conserved leucine-rich repeat motif, a transmembrane domain, and a cytoplasmic Toll/interleukin-1 (TIR) receptor homology signaling domain. Intracellular signaling is activated by agonist binding and is facilitated by the formation of the cytoplasmic TIR domain through heterodimerization with either TLR1 or TLR6. TLR2 is a pattern recognition receptor with the ability to recognize pathogen-associated molecular patterns (PAMPs). Stimulation by PAMPs initiates signaling cascades that activate NF-κB transcription factors inducing the secretion of pro-inflammatory cytokines and effector cytokines directing the immune response.

Expression of toll-like receptor 2 (TLR2) is typically observed in cells involved with the immune response and is associated with a number of related pathologies, including sepsis, inflammation, autoimmune diseases and cancer. TLR2 is broadly expressed among many cancer types and has particularly broad and high expression among pancreatic adenocarcinomas.

The use of synthetic TLR2 agonists for the enhancement of cancer immunotherapy is an active area of research. In an effort to improve the less than 6% 5 year survival rate for pancreatic cancer, the potential of TLR2 ligands for use in targeted pancreatic cancer imaging and treatment have been investigated (Huynh et al., Toll-like Receptor 2 Ligands for Targeted Pancreatic Cancer Imaging and Immunotherapy. *J Med Chem* 2012, 55(22):10.102/jm301002f). Improved survival rates are associated with the surgical resection of the primary tumor if the tumor tissue is completely removed at the margins. However, it is a high risk procedure with a low success rate due to difficulty in clearly identifying tumor tissue from normal tissue, resulting in positive resection margins ($R_1$). The development of new intraoperative surgical methods employing fluorescence guided tumor detection could lead to increased negative resection margins ($R_0$) resulting in improved survival rates. Recent clinical studies involving image-guided surgeries have demonstrated the potential of this approach. Since TLR2 is a bona fide cell surface marker for pancreatic cancer that is highly expressed in 70% of pancreatic tumors but is not highly expressed in surrounding normal pancreas tissue, fluorescence imaging probes developed using TLR2 ligands could be applied to the intraoperative detection of pancreatic tumor margins. Likewise, other probes with TLR2 ligands (e.g., radiolabeled and spin labeled probes) can be used to identify pancreatic tumors. Still further, since other cancers and a number of other pathologies including sepsis, inflammation or inflammatory disorders, and autoimmune diseases, can be targeted with TLR2 ligands, these indications can benefit from TLR2 ligand containing probes.

Thus what are needed are new TLR2 ligands that can be used as targeting moieties for agents to detect or treat pancreatic cancer as well as other cancers, and for other pathologies including sepsis, inflammation or inflammatory disorders, and autoimmune diseases. TLR2 ligands that can be used as an adjuvant for cancer immunotherapy are also needed. Few, if any, potent TLR2 antagonist ligands have been discovered and there is a significant need for such compounds for use in modulation of immune effects and other potential therapeutic uses. The compositions and methods disclosed herein meet these and other needs.

SUMMARY

Disclosed are monoacylated Toll-like receptor 2 ligands, which can be used in targeted agents for the imaging and treatment of pancreatic cancer as well as other cancers, and as an adjuvant for cancer immunotherapy. The monoacylated compounds disclosed herein have a higher binding affinity for TLR2 relative to a known potent diacylated agonists, but only ~½ the bioactivity. Competition of the monoacylated compound with the diacylated compound for binding TLR2 was confirmed. Hence, the reported monoacylated compounds are inhibitors/antagonists of TLR2 activation.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1 is the HPLC chromatogram of purified compound 16. UV absorbance was monitored at 222 nm (shown in dark grey) and 300 nm (shown in light grey).

FIG. 2 is a group of graphs showing the mean competition binding analysis curve generated by in cyto TRF binding assay for Compound 14 and Compound 16 (graph B). Increasing concentrations of compound were added in the presence of 90 nM compound 11 from Huynh et al. using SU.86.86 cells. Compound 14 (graph A) has a $K_i$ of 22 nM ($R^2$=0.90, n=3). Compound 16 (graph B) has a $K_i$ of 16 nM ($R^2$=0.90, n=3).

DETAILED DESCRIPTION

Figure 3A:
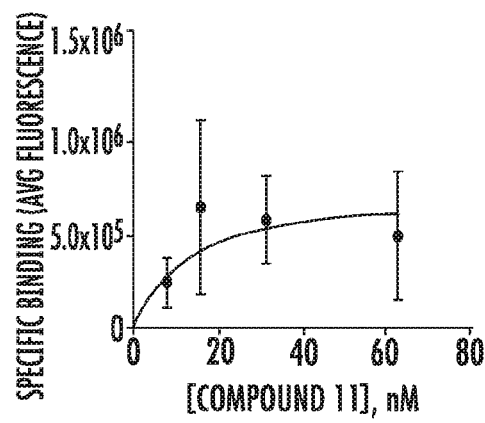
FIG. 3 is a group of graphs. Graph A is the saturation binding curve for HEK293/hTLR2 cells with a $K_d$ of 12±14 nM and $B_{max}$ of 738,713±293,480 AFU ($R^2$=0.7425, n=4 assays×4 replicates). Graph B is the saturation binding curve for the SU.86.86 cells determined a $K_d$ of 55±27 nM and $B_{max}$ of 110,534±31,081 AFU ($R^2$=0.9663, n=5 assays×4 replicates). Graph C is the linear regression plot of fluorescence versus ligand concentration for compound 11 (y=102862X+4.2741), in which the $B_{max}$ value corresponds to 2.853 fmol and 1.0745 fmol per well for HEK293/hTLR2 and SU.86.86 cells, respectively.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula $NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O) $NZ^1Z^2$.

The term "carboxylic acid" as used herein is represented by the formula —C(O)OH. A "carboxylate" or "carboxyl" group as used herein is represented by the formula —C(O) O⁻.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are compounds that can be used to target TLR2 and/or inhibit TLR2 activity. The disclosed TLR2 ligands, which can be used in both targeted agents for the imaging and treatment of pancreatic cancer as well as other cancers, and for treatment of a number of other pathologies including sepsis, inflammation or inflammatory disorders, and autoimmune diseases. From the crystal structure of TLR2 complexes, it was believed that the minimal ligand recognition structure contains a Cys(S-[2,3-bis(palmitoyl) oxy-(R)-propyl] residue. This pharmacophore element was used in Huynh et al, Id., where compound 10, having the diacylated moiety, was found to have potent bioactivity (20 nM EC$_{50}$), high affinity binding (24 nM K$_i$) and effective immune system stimulation. After conjugation of a near-infrared fluorescent dye to this compound high bioactivity (34 nM EC$_{50}$) and binding affinity (11 nM K$_i$) were retained, and tumor specificity was observed in vivo by fluorescence imaging of mice bearing TLR2 expressing tumor xenografts.

Disclosed herein are TLR2 ligands having an S-ethyl-palmitate cysteine residue as shown below:

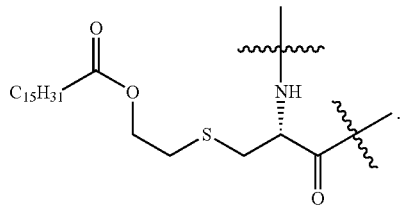

In certain examples, the disclosed compounds can have Formula I

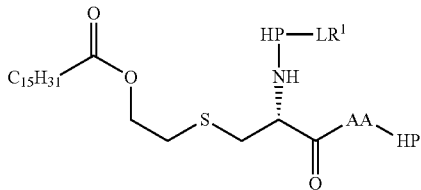

I wherein
L is a bond, H, or linker moiety of 1 to 20 atoms;
R$^1$ is a drug or imaging moiety;
AA is 1 to 2 amino acid residues; and
HP is a hydrophilic polymer.
or a pharmaceutically acceptable salt thereof.

In other specific examples, the disclosed compounds can have Formula I-A

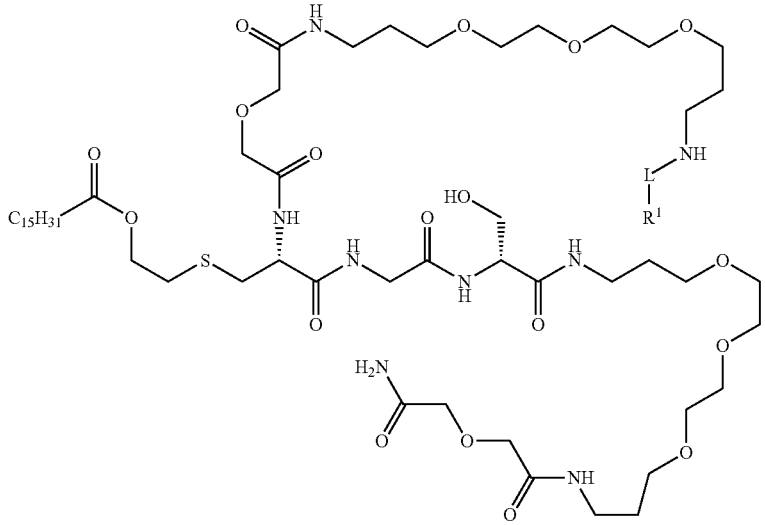

I-A

Specific examples of compounds disclosed herein are

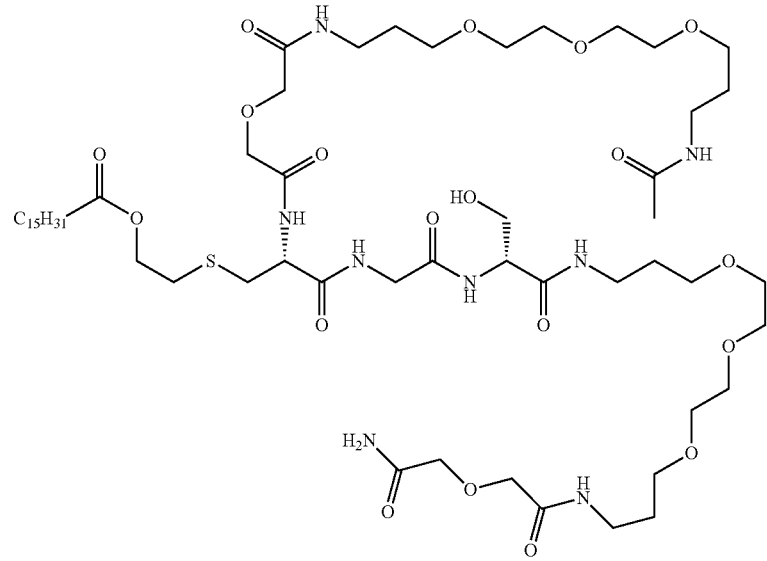

Compound 14

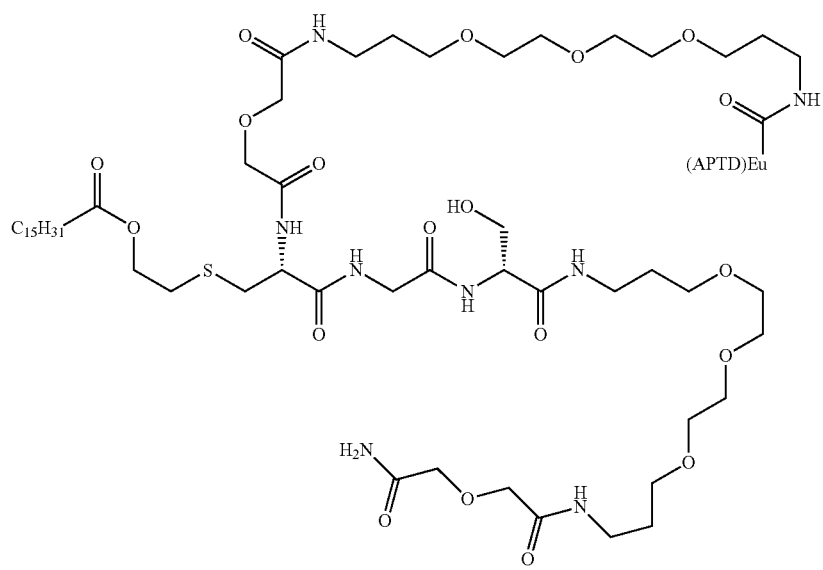

Compound 15 where Eu(DPTA) denotes Europium chelated in diethylenetriaminepentaacetic acid;

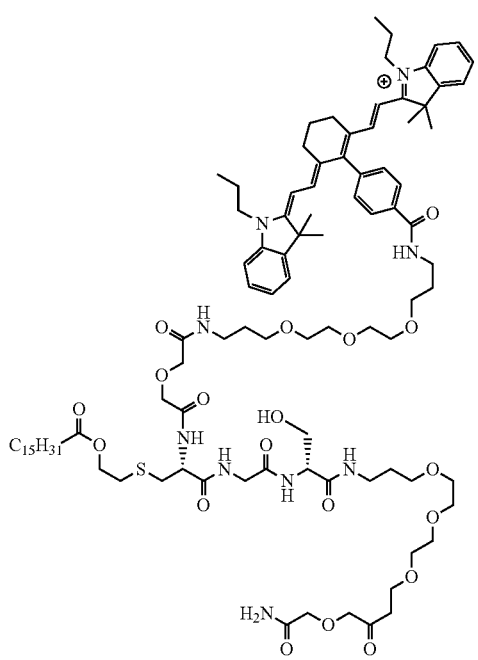

Compound 16

(which contains an IR780 dye moiety)

Linker (L)

The compounds described herein contain a linker (L). The term "linker", as used herein, refers to one or more polyfunctional, e.g., bi-functional or tri-functional molecules, which can be used to covalently couple PEGO moiety to $R^1$. In some embodiments, the linker is flexible. In some embodiments, the linker is stable and biocompatible. The linker can be a single atom, such as a heteroatom (e.g., O, N, or S), a group of atoms, such as a functional group (e.g., amine, —C(=O)—, —CH$_2$—), or multiple groups of atoms, such as an alkylene chain. Suitable linkers include but are not limited to oxygen, sulfur, carbon, nitrogen, alkyl, alkenyl, cycloalkyl, cycloalkenyl, heterocycloalkyl, alkoxyl, aryl, heteroaryl, ether, amine, diamine, amide, alkylamine, thioether, carboxylates, polymer, derivatives or combinations thereof.

The linker can be $R^{14}$, C(O)$R^{14}$C(O), C(O)O$R^{14}$OC(O), C(O)$R^{14}$N, C(O)O$R^{14}$NH, NH$R^{14}$NH, or C(O)NH$R^{14}$NHC(O), C(S)O$R^{14}$OC(S); wherein $R^{14}$ is O, S, $C_1$-$C_{20}$ alkyl; $C_1$-$C_{20}$ heteroalkyl; $C_1$-$C_{20}$ alkylamine; $C_1$-$C_{20}$ alkoxyl; $C_1$-$C_{20}$ alkanoyloxyl; or $C_1$-$C_{20}$ alkylamido, any of which can be optionally substituted with one or more substituents including halogen, alkoxyl, alkyl, alkenyl, cycloalkyl, cycloalkenyl, heterocycloalkyl, aryl, heteroaryl, amine, cyano, nitro, hydroxyl, carbonyl, acyl, carboxylic acid (—COOH), —C(O)$R^{12}$, —C(O)O$R^{12}$, carboxylate (—COO$^-$), primary amide (e.g., —CONH$_2$), secondary amide (e.g., —CONH$R^{12}$), C(O)N$R^{12}R^{13}$, —N$R^{12}R^{13}$, —N$R^{12}$S(O)$_2R^{13}$, —N$R^{23}$C(O)$R^{13}$, —S(O)$_2R^{12}$, —S$R^{12}$, and —S(O)$_2$N$R^{12}R^{13}$, sulfinyl group (e.g., —SO$R^{12}$), and sulfonyl group (e.g., —SOO$R^{12}$); wherein $R^{12}$ and $R^{13}$ can each independently be hydrogen, halogen, hydroxyl, alkyl, haloalkyl, alkenyl, alkynyl, cycloalkyl, heterocycloalkyl, aryl, heteroaryl, carbonyl, cyano, amino, alkylamino, dialkylamino, alkoxyl, aryloxyl, cycloalkyl, alkoxycarbonyl, aminocarbonyl, alkylaminocarbonyl, or dialkylaminocarbonyl.

In some embodiments, the linker is N$R^{14}R^{15}R^{16}$ or (CH)$R^{14}R^{15}R^{16}$; wherein the PEGO moiety or $R^1$ are bonded to at least one of $R^{14}R^{15}R^{16}$, and wherein $R^{14}$, $R^{15}$, and $R^{16}$ are each independently hydrogen, $C_1$-$C_{20}$ alkyl; $C_1$-$C_{20}$ heteroalkyl; $C_1$-$C_{20}$ alkylamine; $C_1$-$C_{20}$ alkoxy; $C_1$-$C_{20}$ alkanoyloxy; or $C_1$-$C_{20}$ alkylamido; any of which can be optionally substituted with one or more substituents independently selected from the group consisting of halogen; hydroxyl; cyano; nitro; amino; alkylamino; dialkylamino; amido; alkylamido; =O; —S(O)$_2$; —SO—; —S—; —S(O)$_2$N—; haloalkyl; hydroxyalkyl; carboxy; alkoxy; aryloxy; alkoxycarbonyl; aminocarbonyl; alkylaminocarbonyl; and dialkylaminocarbonyl. For example, the linker is —(C(O)R$^{14}$)$_3$N, —(R$^{14}$)$_3$N, —(S(O)$_2$R$^{14}$)$_3$N, —(C(O)R$^{14}$)$_3$CH, —(R$^{14}$)$_3$CH, or —(S(O)$_2$R$^{14}$)$_3$CH. In some embodiment, C$_{1-20}$ refers to alkyl groups containing 1, 2, 3, 4, 5, 6, 7, 8, 9, 10, 11, 12, 13, 14, 15, 16, 17, 18, 19, or 20 carbons.

In some embodiments, the linker is —(CO—R$^{14}$)$_2$NH, —(R$^{14}$)$_2$NH, —(SO$_2$R$^{14}$)$_2$NH, —(SOR$^{14}$)$_2$NH, —(OR$^{14}$)$_2$NH, —(O—CO—R$^{14}$)$_2$NH, —(CO—O—R$^{14}$)$_2$NH, —(CO—R$^{14}$)$_2$CH$_2$, —(R$^{14}$)$_2$CH$_2$, —(SO$_2$R$^{14}$)$_2$CH$_2$, —(SOR$^{14}$)$_2$CH$_2$, —(O—CO—R$^{14}$)$_2$CH$_2$, or —(OR$^{14}$)$_2$CH$_2$.

Amino Acids

In some embodiments, the linker can be an amino acid. The amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Examples of suitable amino acids include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, a derivative, or combinations thereof.

Aminodicarboxylic Acids

In some embodiments, the linker is an amino dicarboxylic acid. In some embodiments, the amino dicarboxylic acid can have from 2 to 30 carbon atoms. Examples of suitable amino dicarboxylic acids include, but are not limited to, 1,6-dicarboxylic-2-amino hexanoic acid, 1,7-dicarboxylic-2-amino heptanoic acid, 1,8-dicarboxylic-2-amino octanoic acid, α-aminosuccinic acid, β-aminoglutaric acid, β-aminosebacic acid, 2,6-piperidine dicarboxylic acid, 2,5-pyrrole dicarboxylic acid, 2-carboxypyrrole-5-acetic acid, 2-carboxypiperidine-6-propionic acid, 2-aminoadipic acid, 3-aminoadipic acid, α-aminoazelaic acid, and 4-aminobenzene-1,3-dicarboxylic acid.

Dicarboxylic Acids and Derivatives

In some embodiments, the linker can be a dicarboxylic acid. In some embodiments, the dicarboxylic acid can have from 2 to 20 carbon atoms. Examples of dicarboxylic acid include, but are not limited to, butanedioic acid, pentanedioic acid, hexanedioic acid, heptanedioic acid, octanedioic acid, nonanedioic acid, decanedioic acid, undecanedioic acid, dodecanedioic acid, tridecanedioic acid, 1,12-dodecanedicarboxylic acid, 1,15-pentadecanedicarboxylic acid, hexadecanedioic acid, and 1,15-pentadecanedicarboxylic acid. In some embodiments, the dicarboxylic acid is an halogenated dicarboxylic acid, hydroxy dicarboxylic acid, or ether dicarboxylic acid.

Tricarboxylic Acids and Derivatives

In some embodiments, the linker can be a tricarboxylic acid or a derivative thereof. In some embodiments, the tricarboxylic acid can have from 2 to 30 carbon atoms. The tricarboxylic acid can be aliphatic or cyclic. Examples of tricarboxylic acid include, but are not limited to, 2-phosphonobutane-1,2,4-tricarboxylic acid and 1,2,3-propane tricarboxylic acid.

Alcohols

In some embodiments, the linker can be an alcohol or a derivative thereof. The alcohol can be a diol, triol, amino alcohol, amino dialcohol, amino trialcohol, ethylene glycol, propylene glycol, or a derivative. In some embodiments, the alcohol can have from 2 to 30 carbon atoms. Examples of suitable alcohols include, but are not limited to, triethanolamine, 2-aminoethanol, diisopropanolamine, triisopropanolamine, amino hexanol, 2-[(2-methoxyethyl)methylamino]-ethanol, propanolamine, N-methylethanolamine, diethanolamine, butanol amine, isobutanolamine, pentanol amine, 1-amino-3-(2-methoxyethoxy)-2-propanol, 2-methyl-4-(methylamino)-2-butanol, 6-amino-1-hexanol, heptaminol, isoetarine, norepinephrine, sphingosine, phenylpropanolamine, derivatives, and combinations thereof.

Polymers

In other embodiments, the linker can be a polymer. A wide variety of polymers and methods for forming the polymers are known in the art of polymer science. Polymers can be degradable or non-degradable polymers. Polymers can be natural or unnatural (synthetic) polymers. Polymers can be homopolymers or copolymers comprising two or more monomers. In terms of sequence, copolymers can be random, block, or comprise a combination of random and block sequences. The polymers can in some embodiments be linear polymers, branched polymers, or hyperbranched/dendritic polymers. The polymers can also be present as a crosslinked particle or surface functionalized inorganic particle. Suitable polymers include, but are not limited to poly(vinyl acetate), copolymers of styrene and alkyl acrylates, and copolymers of vinyl acetate and acrylic acid, polyvinylpyrrolidone, dextran, carboxymethylcellulose, polyethylene glycol, polyalkylene, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB), poly-4-hydroxybutyrate (P4HB), polycaprolactone, polyacrylates and polymethacrylates; polyanhydrides; polyorthoesters; polysytyrene (PS), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pBMAD), poly(butadiene maleic anhydride-co-phenylalanine), poly(butadiene maleic anhydride-co-tyrosine), poly(bis carboxy phenoxy propane-co-sebacic anhydride) (poly(CCP:SA)), alginate; and poly(fumaric anhydride-co-sebacic anhydride (p[FA:SA]), copolymers of p[FA:SA], polyacrylates, and polyacrylamides, and copolymers thereof, and combinations thereof.

Other suitable linkers include, but are not limited to, diamino compounds such as ethylenediamine, 1,2-propylenediamine, 1,5-pentanediamine, 1,6-hexanediamine, and the like.

R$^1$

The disclosed compounds can also contain one or more drug or imaging moiety moieties, R$^1$. In some embodiments, the imaging moiety can be the drug. Mixtures of compounds are also disclosed, e.g., where some contain an imaging moiety and others contain a drug moiety, or where different imaging moieties and/or different drug moieties are used.

Imaging Moiety

The imaging moiety can contain any detectable label. Examples of suitable detectable labels include, but are not limited to, a UV-Vis moiety, a near-infrared moiety, a luminescent moiety, a phosphorescent moiety, a magnetic spin resonance moiety, a photosensitizing moiety, a photocleavable moiety, a chelating center, a heavy atom, a radioactive isotope, an isotope detectable spin resonance moiety, a paramagnetic moiety, a chromophore, or any combination thereof. In a specific example, the imaging moiety is a fluorescent moiety. In some embodiments, the label is detectable without the addition of further reagents.

In some embodiments, the imaging moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The imaging moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris(4,7-diphenyl-1,10-phenanthroline) (Ru (dpp)$_3$); Ru (II) tris(1,10-phenanthroline) (Ru(phen)$_3$), tris(2,2'-bipyridine)ruthenium (II) chloride hexahydrate (Ru (bpy)$_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

The imaging moiety can contain a radiolabel, also referred to herein as radioisotope. The radiolabel can also be a therapeutic moiety, i.e., a radiolabel comprising a therapeutic radionuclide such as, $^{90}$Y, $^{177}$Lu or $^{225}$Ac. Other examples of suitable radiolabels include, but are not limited to, metal $^{18}$F, $^{64}$Cu, $^{67}$Cu, $^{68}$Ga, $^{89}$Zr, $^{111}$In, $^{124}$I, $^{123}$I, and $^{99m}$Tc. In some embodiments, the radiolabel can be chelated by a macrocyclic molecule. Examples of such macrocyclic molecules include, but are not limited to, 2,2',2''-(10-(2-((2,5-dioxopyrrolidin-1-yl)oxy)-2-oxoethyl)-1,4,7,10-tetraaza-cyclododecane-1,4,7-triyl)triacetic acid (DOTA)-based chelators, diethylene triamine pentaacetic acid (DTPA)-based chelators, and a derivative or a combination thereof. The imaging moiety could also include Gadolinium chelates encapsulated in nanoparticle formulations.

The imaging moiety can contain a magnetic spin resonance label. Examples of suitable spin resonance label include free radicals such as nitroxide-stable free radicals. Stable free radicals of nitroxides are known in the art, see for example Keana, "Newer Aspects of Synthesis and Chemistry of Nitroxide Spin Labels", Chemical Reviews, 1978, Vol. 78 No. 1, pp. 37-64, which disclosure is incorporated herein by reference. Suitable nitroxides include, but are not limited to, those derived from 2,2,6,6-tetramethylpiperidine-N-oxyl (TEMPO), 2,2,5,5-tetramethylpyrroline-N-oxyl, and 4,4-dimethyloxazolidine-N-oxyl which is a doxyl nitroxide. All of these compounds are paramagnetic and hence capable of excitation or changes in magnetic resonance energy levels and therefore provide imaging. Other nitroxides include, but are not limited to, doxyl nitroxides, proxyl nitroxides, azethoxyl nitroxides, imidazoline derived nitroxides, tetrahydrooxazine derived nitroxides, and the recently synthesized steroid nitroxides, and the like.

Spin labeling, as used herein, is understood to mean "spin label" as that is defined in the Keana article, namely when a nitroxide bearing molecule that is covalently attached to another molecule of interest, the nitroxide grouping does not significantly disturb the behavior of the system under study. Thus, the nitroxide molecule being paramagnetic, simply enhances the energy or excitation level subjected to the magnetic field during the magnetic resonance.

Drug Moiety

The disclosed compounds can also contain a drug. The TLR2 antagonist ligands can be used alone as inhibitor therapy, can be linked to a therapeutic moiety, or can be used in combination with other existing therapies. Drug refers to a group that when administered to a subject, will cure, or at least relieve to some extent, one or more symptoms of, a disease or disorder. Therapeutic moiety include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included. In addition, therapeutic moiety includes those agents capable of direct toxicity and/or capable of inducing toxicity towards healthy and/or unhealthy cells in the body. Also, the therapeutic moiety may be capable of inducing and/or priming the immune system against potential pathogens. A number of mechanisms are possible including without limitation, (i) a radioisotope linked to a protein as is the case with a radiolabeled protein, (ii) an antibody linked to an enzyme that metabolizes a substance, such as a prodrug, thus rendering it active in vivo, (iii) an antibody linked to a small molecule therapeutic agent, (iv) a radioisotope, (v) a carbohydrate, (vi) a lipid, (vii) a thermal ablation agent, (viii) a photosensitizing agent, and (ix) a vaccine agent.

The drug or imaging moiety can be one that kills or inhibits cancer cells directly (e.g., cisplatin) or it can be one that can kill or inhibit a cancer cell indirectly (e.g., gold nanoparticles that kill or destroy cancer cells when heated using a light source). In one aspect, the compounds can include therapeutic moieties including without limitation small molecules or drugs.

In other examples, compounds disclosed herein can be represented as Formula I where $R^1$ is an azide. These compounds can be used as reagents for forming conjugates by click chemistry. Thus, the practitioner can add imaging agents or drugs of their choice, which contain or are modified to contain a dipolarophile, by contacting them with a compound as disclosed herein where $R^1$ is an azide.

Hydrophilic Polymer (HP)

The hydrophilic polymer can be PVA, PEG, polyacrylamide, acetates, PEO, PEA, PVP, PDX, and variations thereof. The length of the HP moiety can be from 10 to 100 atoms in length, e.g., from 10 to 25, from 10 to 50, from 25 to 50, from 25 to 75 or from 50 to 100 atoms in length. In one specific example, the hydrophilic polymer can be a short PEG oligomer (PEGO).

Amino Acids (AA)

The amino acid moiety (AA) can be any one or two amino acids chosen from alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, 5,5,5-trifluoroleucine, α-aminohexanoic acid, thiaproline, and hexafluoroleucine. In a specific example, the amino acid moiety can be glycine-D-serine.

Methods of Synthesis

The S-ethylpalmitate cysteine residue can be prepared by several routes. Scheme 1 shows a representative synthesis of palmitic ester.

Scheme 1

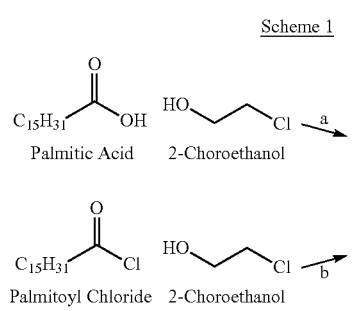

(a) 1.2 eq. DCC, 5% DMAP, DCM, 95%
(b) DCM, TEA, 92%

2-iodoethylpalmitate can be used as well and can be prepared from 2-iodoethanol. The cysteine monomer can be synthesized from at least three different routes. These are shown respectively in Schemes 2-4.

Scheme 2

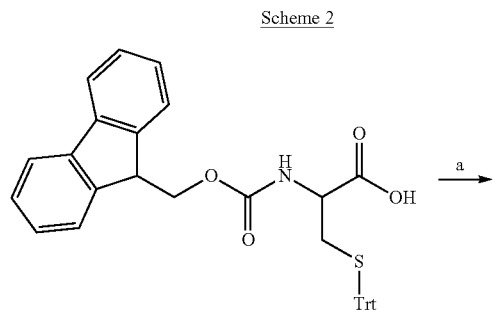

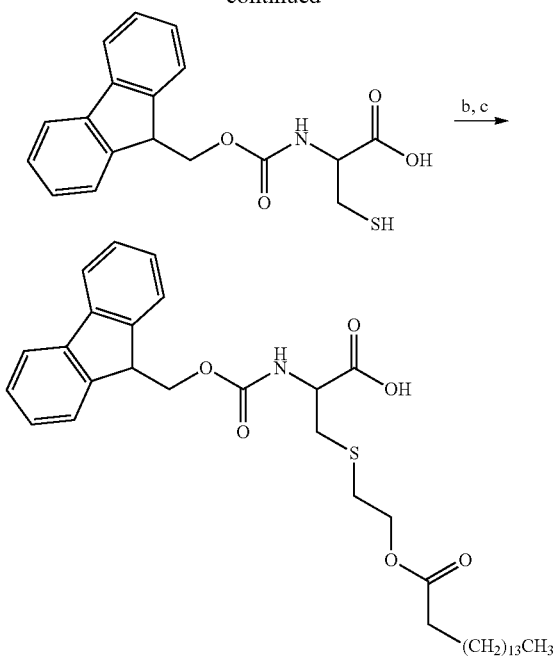

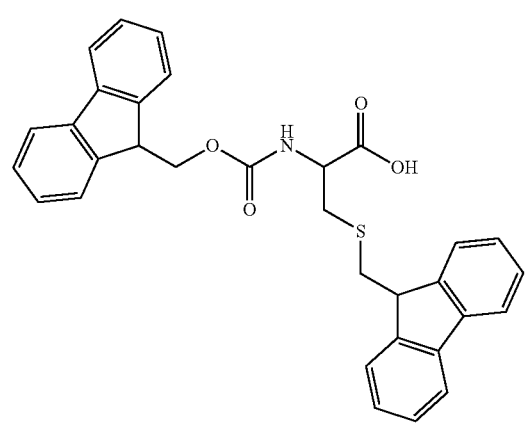

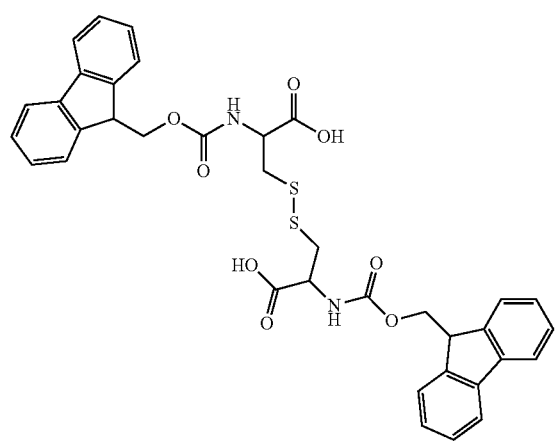

(a) 5% TFA, 3% Triethylsilane, DCM, quant.
(b) TMS—Cl, TEA
(c) Base, Chloropalmitoylester

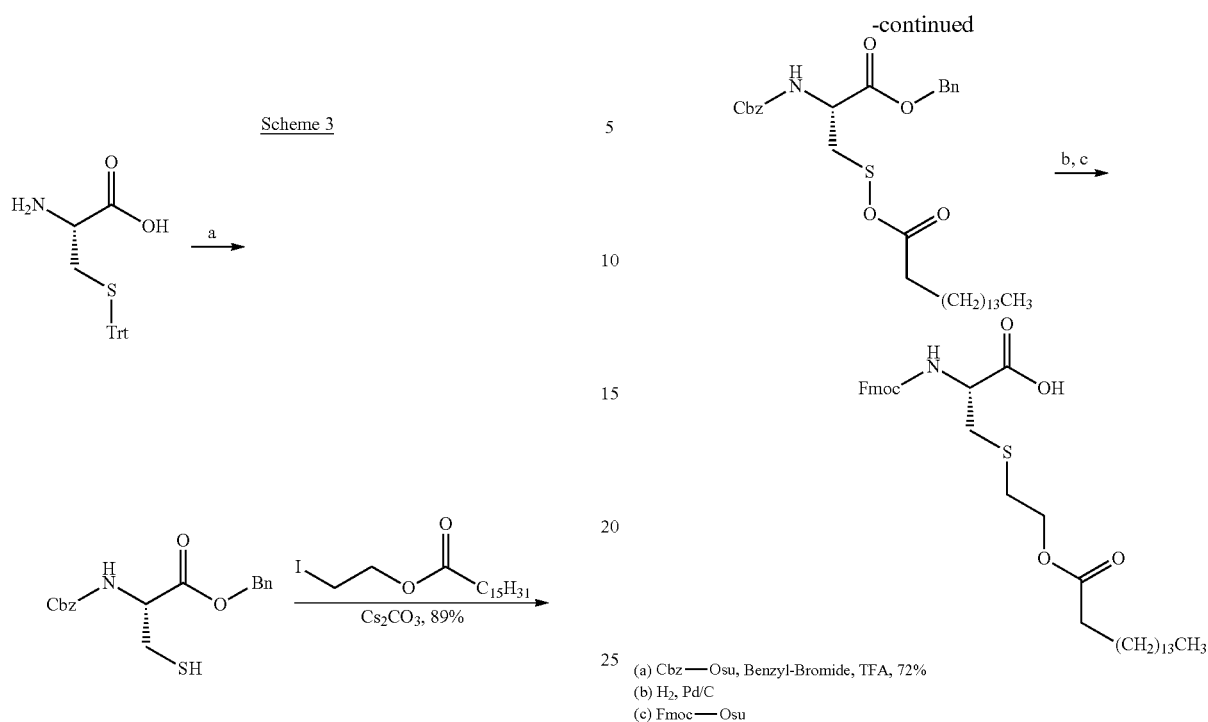
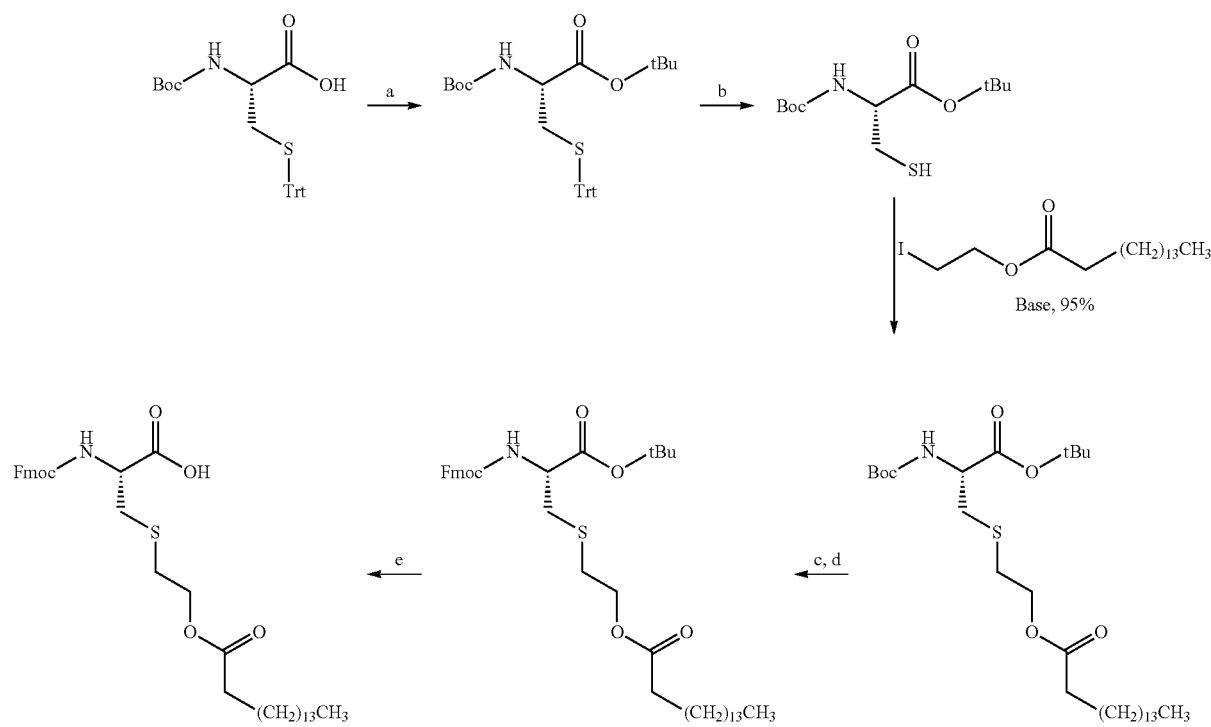

The synthesis can be completed using Fmoc-protected solid phase peptide synthesis strategy as shown in Scheme 5 for the IR780 conjugate (compound 16). Other compounds disclosed herein can be prepared by similar techniques.
Methods of Use
Also described herein are methods of using the compositions disclosed herein. The compositions can be used to
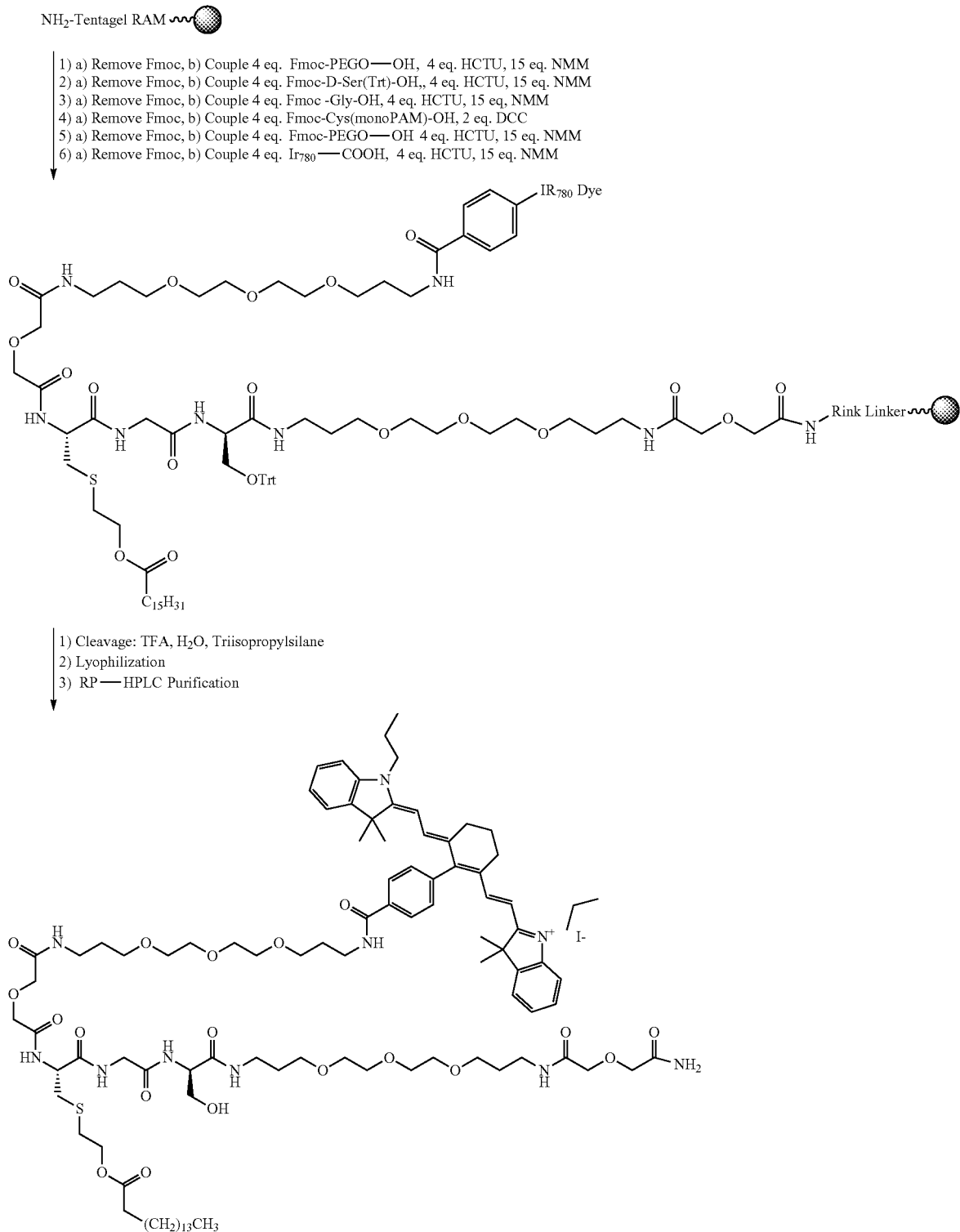
Scheme 5 label cancer cells and tumors for identification and characterization. The compositions can also be used for treating a cancerous tissue.

Generally, the disclosed methods include contacting the cancer cell with an effective amount of the compositions as described herein. One of skill in the art recognizes that an amount can be considered therapeutically effective even if the condition is not totally eradicated but improved partially. The compositions can be injected directly into the target tissue, or can be administered systemically. More specifically, the compositions can be administered using any suitable method including intravenous (i.v.), intraperitoneal (i.p.), intramuscular (i.m.), intratumoral (i.t.), intraarterial (i.a.), topically, and/or inhalation. Intravenous administration is particularly preferred for solid tumors, while i.p. administration is preferred for pancreatic, liver, and gastric tumors. Advantageously, even when administered systemically, the compositions preferentially accumulate at the cancerous tissue, as opposed to surrounding healthy tissue.

The disclosed compounds can contain an imaging moiety and/or therapeutic moiety that kills or inhibits an infected, dysfunctional, or abnormal cell and/or tissue directly. In some embodiments, the method involves image guided surgery using a compound comprising an imaging moiety to detect and resect cancer from a subject followed by the use of the same or a different compound to kill the remaining cancer cells. The composition can be administered before, during, and/or after a tumor resection procedure. For example, one can administer a compound as disclosed herein to a subject, irradiate a region to identify the cancer, and surgically remove the cancer.

Further provided herein are methods of treating cancer in a subject comprising administering to the subject an effective amount of a compound or composition as disclosed herein. The disclosed compounds bind TLR2 and thus are particularly well suited for cancers where TLR2 is expressed or overexpressed. There are a large number of tumors that have high TLR2 expression. Indeed, nearly every cancer type has a sub-set of tumor types with high TLR2 expression. Some examples of such cancers are colorectal cancer, ovarian cancer, lung cancer, melanoma, brain cancer, breast cancer, hepatocellular carcinoma, laryngeal cancer, pancreatic adenocarcinoma, stomach cancer, liver cancer, prostate cancer, acute myeloid leukemia, and gastric cancer. Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor. In a preferred aspect, the cancer is pancreatic cancer since in pancreatic adenocarcinomas, 70%, have robust TLR2 expression.

Additionally, the method can further comprise administering an effective amount of ionizing radiation to the subject and/or another anti-cancer compound. Also disclosed are methods of imaging a cancer cell comprising contacting the cell with a compound as disclosed herein.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

The disclosed compounds can also be used to treat or diagnose sepsis, acute inflammation, chronic inflammation (arthritis), chronic obstructive pulmonary disease, cardiovascular disease, autoimmune diseases, vaccines, ant-viral activity, Parkinson's (neurodegenerative disorders), influenza.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil, gemcitabine or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied as a liquid or solid. However, it will generally be desirable to administer them topically to the skin as compositions, in combination with a dermatologically acceptable carrier, which can be a solid or a liquid.

Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one inhibitor compound or composition disclosed herein, e.g., any compound of Formulas I. A packaged dosage formulation can optionally comprise in one or more containers a pharmaceutically acceptable carrier or diluent. A packaged dosage formulation can also optionally comprise, in addition to an inhibitor compound or composition disclosed herein, other TLR2 ligands, or an immunotherapeutic such as ipilimumab.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Materials and Reagents: $N^\alpha$-Fmoc protected amino acids, HBTU, and HOBt were purchased from SynPep (Dublin, Calif.), from Novabiochem (San Diego, Calif.), or ChemImpex (Wood Dale, Ill.). Rink amide Tentagel S resin was acquired from Rapp Polymere (Tubingen, Germany). HCTU, HOBt, DIC and DIEA were purchased from IRIS Biotech (Marktredwitz, Germany) or ChemImpex (Wood Dale, Ill.). The following side chain protecting groups were used for the amino acids DSer (tBu). An Fmoc-protected version of PEGO (19-amino-5-oxo-3,10,13,16-tetraoxo-6-azanonadecan-1-oic acid) was purchased from Novabiochem. IRDye800CW maleimide was provided by LI-COR (Lincoln, Nebr.). IRDye780 and 4-carboxyphenylboronic acid was purchased from Sigma Aldrich (St. Louis, Mo.). Peptide synthesis solvents, dry solvents, and solvents for HPLC (reagent grade) were acquired from VWR (West Chester, Pa.), Sigma-Aldrich (Milwaukee, Wis.), or ChemImpex (Wood Dale, Ill.) and were used without further purification unless otherwise noted. The C-18 Sep-Pak™ Vac RC cartridges for solid phase extraction were purchased from Waters (Milford, Mass.). The C-8 HPLC columns were purchased from AAPPTec (Louisville, Ky.).

Cell Culture: SU.86.86 pancreatic adenocarcinoma cells (ATCC CRL-1837) were grown in RPMI 1640 media (Life Technologies Gibco) supplemented with 10% NCS. The HEK293/hTLR2 cells (InvivoGen, San Diego, Calif.) were cultured in DMEM/F12 medium supplemented with 10% NCS, 1% penicillin/streptomycin solution, 10 μg/mL blasticidin (InvivoGen). All cells were grown at 37° C. and 5% $CO_2$. SU.86.86 cells express endogenous levels of TLR2 (Morse et al., Identification of novel pancreatic adenocarcinoma cell-surface targets by gene expression profiling and tissue microarray. *Biochem Pharmacol* 80(5):748-54).

Animals: All procedures were in compliance with the Guide for the Care and Use of Laboratory Animal Resources (1996), National Research Council, and approved by the Institutional Animal Care and Use Committee, University of South Florida, under the approved protocols R0946. Immunocompromised mice were housed in a clean facility with special conditions that include HEPA filtered ventilated cage systems, autoclaved bedding, autoclaved housing, autoclaved water, irradiated food, and special cage changing procedures. Mice were handled under aseptic conditions including the wearing of gloves, gowns, and shoe coverings. Mice were anesthetized by inhaled isofluorane gas and remained anesthetized for the minimum amount of time required for imaging studies, ranging from 3 to 45 min at a time.

Compound Synthesis

Compounds were prepared by solid-phase synthesis on Rink Amide Tentagel resin (0.23 mmol/g) using Fmoc/tBu synthetic strategy and standard DIC-HOBt and HBTU or HCTU activations (Krchnak et al., Noninvasive continuous monitoring of solid-phase peptide synthesis by acid-base indicator. *Int J Pept Protein Res* 1988, 32(5):415-6; Krchnak et al., Color-monitored solid-phase multiple peptide synthesis under low-pressure continuous-flow conditions. *Pept Res* 1990, 3(4):182-93; Vagner et al., Heterobivalent ligands crosslink multiple cell-surface receptors: the human melanocortin-4 and delta-opioid receptors. *Angew Chem Int Ed Engl* 2008, 47(9):1685-8). The synthesis was performed in fritted syringes using a Domino manual synthesizer obtained from Torviq (Niles, Mich.) or using a T-Bore manual Peptide Synthesis Vessel with medium frit from ChemGlass (Vineland, N.J.). For compounds 14, 15, and 16 an Fmoc-protected version of PEGO (Novabiochem, San Diego, Calif.) was used and an Fmoc protected derivative of Cys, Fmoc-Cys(S-[palmitoyloxyethyl])-OH (Fmoc-Cys(Poe)-OH) was synthesized.

The resin was swollen in THF for an hour, washed with DMF, and the Fmoc protecting group removed with 20% piperidine in DMF (2 min+20 min). The resin was washed with DMF (3×), DCM (3×), 0.2 M HOBt in DMF (2×), and finally with DMF (2×) and the first amino acid coupled using pre-activated 0.3 M HOCt ester in DMF (3 eq. of $N^\alpha$-Fmoc amino acid, 3 eq. of HO and 6 eq. of DIC). An on-resin test using Bromophenol Blue was used for qualitative and continuous monitoring of reaction progress. To avoid deletion sequences and slower coupling rate in longer sequences, the double coupling was performed at all steps with 3 eq. of amino acid, 3 eq. of HBTU and 6 eq. of DIEA in DMF. Whenever beads still tested Kaiser positive, a third coupling was performed using the symmetric anhydride method (2 eq. of amino acid and 1 eq. of DIC in dichloromethane). Any unreacted $NH_2$ groups on the resin thereafter were capped using an excess of 50% acetic anhydride in pyridine for 5 min. When the coupling reaction was finished, the resin was washed with DMF, and the same procedure was repeated for the next amino acid until all amino acids were coupled. Fmoc-PEGO was attached to the resin as symmetrical anhydride (6 eq of acid and 3 eq of DIC in DCM-DMF).

A cleavage cocktail (10 mL per 1 g of resin) of TFA (91%), water (3%), triisopropylsilane (3%), and 1,2-ethylenedithiol (3%) was injected into the resin and stirred for 4 h at room temperature. Alternatively, a cleavage cocktail of 90% trifluoroacetic acid (5% water, and 5% triisopropylsilane) was used. The crude ligand was isolated from the resin by filtration, the filtrate was reduced to low volume by evaporation using a stream of nitrogen, and the ligand was precipitated in ice-cold diethyl ether, washed several times with ether, dried, dissolved in water and lyophilized to give off-white solid powders that were stored at −20° C. until purified.

Purity of the peptides was ensured to >95% purity using analytical HPLC (Waters Alliance 2695 separation model with a dual wavelength detector Waters 2487 or Dionex**) with a reverse-phase column (Waters Symmetry, 3.0·75 mm, 3.5 μm; flow rate=0.3 mL/min). HPLC conditions were as follows: HPLC pH 2, linear gradient from 10 to 90% B over 30 min, where A is 0.1% TFA and B is acetonitrile or THF, HPLC pH 6, linear gradient from 10 to 90% B over 30 min, where A is 0.1% TEAA and B is acetonitrile or THF. Compound 16 was purified with a linear gradient of 25-100% B over 50 min, where A is $H_2O$+0.1% TFA and B is methanol+0.1% TFA. Size exclusion chromatography was performed on a borosilicate glass column (2.6×250 mm, Sigma, St. Louis, Mo.) filled with medium sized Sephadex G-25 or G-10. The compounds were eluted with an isocratic flow of 1.0 M aqueous acetic acid.

Solid-Phase Extraction (SPE) was employed where simple isolation of final compound was needed from excess salts and buffers for e.g., lanthaligand synthesis. For this purpose, C-18 Sep-Pak™ cartridges (100 mg or 500 mg) were used and pre-conditioned initially with 5 column volumes (5 times the volume of packed column bed) each of acetonitrile, methanol, and water, in that order. After loading the compound, the column was washed several times with water, and then gradually with 5, 10, 20, 30, 50, and 70% of aqueous acetonitrile to elute the peptide.

Structures were characterized by ESI (Finnigan, Thermoquest LCQ ion trap instrument), MALDI-TOF or FT-ICR mass spectrometry (Table 1). An appropriate mixture of standard peptides was used for internal calibrations. The test compounds were dissolved in DMSO at a 1 mg/mL concentration as stock solutions stored at −20° C. For biological experimental use, 10 μg/mL working solutions of the compounds were prepared from stock solutions in sterilized, deionized water and used immediately.

TABLE 1

Mass spectral data and HPLC retention times.

| No. | Structure | Rt (k') | Calcd [MH+] | Exp. [MH+] |
|-----|-----------|---------|-------------|------------|
| 14 | Ac-Pego-Cys(S-[palmitoyloxyethyl])-Gly-DSer-PEGO-NH$_2$ | 10.0 | 1225.72 | 1225.5 |
| 15 | (Eu)DTPA-Pego-Cys(S-[palmitoyloxyethyl])-Gly-DSer-PEGO-NH$_2$ | 8.98 | 1706.74 1708.74 (Eu$^{+2}$) | 1706.4, 1708.4, 1728.5, 1730.5 (Na) |
| 16 | IR780-Pego-Cys(S-[palmitoyloxyethyl])-Gly-DSer-PEGO-NH$_2$ | 20.8 | 1790.07 1790.0 16 (M$^+$) 989 | |

[a] Peptide was eluted with a linear MeCN/0.1% $CF_3CO_2H$ aqueous gradient (10% to 90% in 30 min) at a flow rate of 0.3 mL/min); Waters XBridge C-18 column (3.0 × 150 mm, 3.5 μm); HPLC k' = (peptide retention time − solvent retention time)/solvent retention time. All the obtained purified peptides showed >95% purity.
[b] MS found molecular peaks MH$^+$; high resolution Bruker Reflex III MALDI-TOF instrument.
[c] Compound 16 was eluted with a linear gradient of MeOH/0.1% $CF_3CO_2H$ aqueous gradient (15-100% in 20 min) at a flow rate of 1 mL/min and 40° C.; AAPPTec Spirit Protein C-8 column (250 × 46 mm, 5 μm). Monoisotopic mass (M$^+$) of compound 16 was measured with Applied Biosystems 4700 MALDI TOF/TOF (Table 1).

Synthesis of (Eu)DTPA Labeled Compound 15

DTPA was attached to H-PEGO-Dhc(Poe)-Gly-DSer-PEGO-resin as follows. DTPA anhydride (3 equiv.) and HOBt (3 equiv.) in DMSO were heated until dissolved (60° C.) then stirred for 30 min at room temperature. The preformed DTPA-OBt diester was injected into the free-amine H-PEGO-Cys(Poe)-Gly-DSer-PEGO-resin and stirred overnight. The resin was washed with DMSO, THF, 5% DIEA 5% water in THF (5 min), THF, and DCM. The compound was cleaved from the resin as described above and purified by HPLC. The purified peptide was dissolved in 0.1 M ammonium acetate buffer pH 8.0, 1.1 eq. Eu(III)Cl$_3$ was added and the reaction was stirred at room temperature overnight. The Eu-labeled peptide was separated using Solid-Phase Extraction (SPE) and lyophilized to yield an amorphous white powder. The final compound was characterized by HPLC (TEAA buffer pH 6.0), ESI-MS and/or FT-ICR (Table 1).

Synthesis of IRDye800CW-labeled Compound 17

Attachment of Trt-Mpr-OH (S-trityl-3-mercaptopropionic acid) to the N-terminus H-PEGO-Cys(Poe) Gly-DSer-PEGO-resin was performed using preformed HBTU activation (3 equiv. of Trt-Mpr-OH, 3 equiv. of HBTU and 6 equiv. of DIEA in DMF). The resin was washed with DMF and DCM. The thiol intermediate was cleaved from the resin as described above and purified by HPLC.

The thiol intermediate H-Mpr-PEGO-Cys(Poe)-Gly-DSer-PEGO-NH$_2$ (1 μmol) was dissolved in 1 mL DMF and reacted with 1 equiv. of IRDye800CW maleimide under argon atmosphere. The reaction was monitored by HPLC and additional aliquots (0.1 equiv.) of dye were added until the reaction complete. The conjugate, compound 6, IRDye800CW-Mpr-PEGO-Cys(Poe)-Gly-DSer-PEGO-NH$_2$, was purified by HPLC.

Synthesis of IRDye780-labeled Compound 16

Infrared dye 780 was reacted through Suzuki coupling with 4-carboxyphenylboronic acid. The dye conjugate was attached to N-terminus of H-PEGO-Cys(Poe) Gly-DSer-PEGO-resin with HCTU activation (3 equiv. of IR780 dye, 3 equiv. of HCTU and 6 equiv. of DIEA in DMF). Crude peptide was cleaved from the resin as described, and the filtrate was concentrated in vacuo. The residue from cleavage was dissolved in 50/50 MeOH, $H_2O$ (v/v) and purified with the MeOH HPLC method as described below. Purified compound 16 was eluted with a linear gradient of MeOH/ 0.1% $CF_3CO_2H$ (B) aqueous gradient (15-100% in 20 min) followed by a 5 min wash of 100% B at a flow rate of 1 mL/min and 40° C.; AAPPTec Spirit Protein C-8 column (250×46 mm, 5 µm). Pure peptide had a retention time (k') of 20.8 min. FIG. 1 shows the HPLC chromatogram of purified compound 16. UV absorbance was monitored at 222 nm (shown in red) and 300 nm (shown in blue).

In Cyto Europium TRF Binding Assays

Europium Time-Resolved Fluorescence (TRF) binding assays were performed as described in Handle et al. with slight modifications using SU.86.86 cells plated in 96-well black plates with white opaque wells (PerkinElmer) (Handl et al., Lanthanide-based time-resolved fluorescence of in cyto ligand-receptor interactions. *Anal Biochem* 2004, 330 (2):242-50; Handl et al., Development of a lanthanide-based assay for detection of receptor-ligand interactions at the delta-opioid receptor. *Anal Biochem* 2005, 343(2):299-307; Josan et al., Solid-phase synthetic strategy and bioevaluation of a labeled delta-opioid receptor ligand Dmt-Tic-Lys for in vivo imaging. *Org Lett* 2009, 11(12):2479-82). Cells were grown in the 96-well plates for 2 days reaching approximately 80% confluency. Competition binding assays were performed to test the TLR2 binding specificity of the test ligand using SU.86.86 cells. On the day of the experiment, the cell culture media was aspirated and 50 µL of nonlabeled test ligand was added in a series of decreasing concentrations (1 µM to 0.01 nM) followed by 50 µL of the competing Eu-labeled ligand 11 (Huynh et al., Novel Toll-like Receptor 2 Ligands for Targeted Pancreatic Cancer Imaging and Immunotherapy. *J Med Chem* 2012) at a fixed concentration of 90 nM. Cells were incubated with labeled and unlabeled ligands for 1 h at 37° C. Following incubation, cells were washed three times to remove unbound ligand. Next, 100 µL of DELFIA Enhancement Solution (PerkinElmer) was added to each well. Cells were incubated for 30 min at 37° C. prior to reading. The plates were read on PerkinElmer VICTOR X4 Multilabel reader using the standard Europium TRF protocol. To determine the mean statistical analysis was performed using GraphPad Prism software. Binding of the monoacyl TLR2 ligand (compound 14 of Table 2) was tested using the (Eu)DTPA chelate version of the diacyl TLR2 ligand (compound 11 used in Huynh et al, Id.) in a time-resolved fluorescence competition binding assay. SU.86.86 pancreatic cells with endogenous expression of TLR2 were used for the assay. Results are shown in Table 2.

TABLE 2

TLR2 Binding Affinity ($K_i$) Determined by Competition Binding Assays in the TLR2 endogenous expressing pancreatic cancer SU.86.86 cell line, SU.86.86.

| Compd | $K_i$ (nM) | Std. Error | $R^2$ Value |
| --- | --- | --- | --- |
| 10 | 91 | 1.4 | 0.95 |
| 14 | 22 | 1.8 | 0.90 |
| 16 | 16 | 1.6 | 0.85 |

The calculated binding affinity of Compound 14 was 22±1.8 nM $K_i$ with a good fit of the data, $R^2$=0.90 (n=3) (FIG. 2, graph A). The calculated binding affinity of Compound 16 was 16±1.6 nM $K_i$ with a good fit of the data, $R^2$=0.85 (n=3) (FIG. 2, graph B). The reported binding affinity for the diacyl ligand (compound 10) was lower with a $K_i$=91 nM in the endogenous TLR2 expressing pancreatic cancer cell line, SU.86.86.

Cell Surface Receptor Number Determination

The number of toll-like 2 receptors expressed on the cell surface of the endogenous TLR2 expressing pancreatic adenocarcinoma cells, SU.86.86, and the genetically engineered TLR2 expressing HEK-293/hTLR2 cells was calculated using an adapted version of the binding assay, as previously described (Huynh et al., Novel Toll-like Receptor 2 Ligands for Targeted Pancreatic Cancer Imaging and Immunotherapy. *J Med Chem* 2012). Increasing amounts of a europium labeled TLR2 ligand, compound 11, were added to cells in 96-well plates. To test nonspecific binding, cells were preincubated with 1 µM $Pam_2CSK_4$ (Invivogen) prior to the addition of labeled ligand. The data were fit with GraphPad Prism software using the nonlinear regression, one-site binding equation. Each data point indicates the average of four assays with 4 replicates, with error bars indicating the standard error of the mean. To calculate the number of receptors per cell, standard curves of the relationship between fluorescence intensities and ligand concentrations were generated. Increasing amounts of Eu-TLR2 ligand, compound 11, were added to wells of 96-well plate containing Delfia Enhancement solution in quadruplicate. The plate was then incubated at 37° C. for 30 min then read using Perkin Elmer plate reader using the standard Europium protocol. GraphPad Prism was used to plot the standard curves. The standard curves were then used to determine the amount of ligand present at the $B_{max}$ obtained in the saturation binding assay. The average number of cells per well at the end of the assay was calculated. To determine the receptor number, the following equation was used: (Eu amount for $B_{max}$ (mole)/avg cell number per well)×6.023× $10^{23}$=receptor number per cell.

Figure 3B:
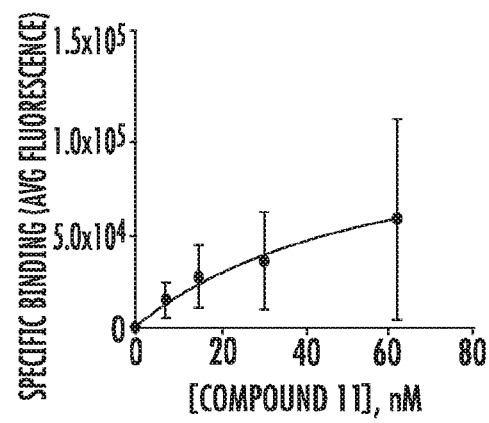
Figure 3C:
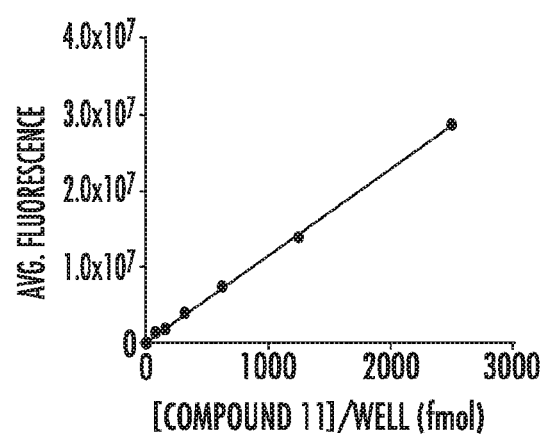
Figure 4A:
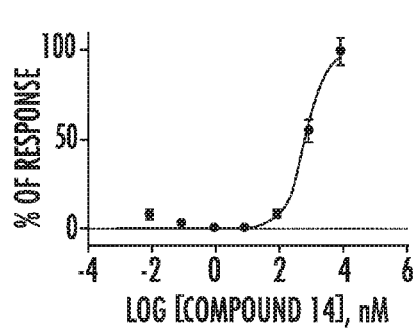
FIG. 4 is a group of graphs. Graph A, is a dose-response curve that was generated by measuring the TLR2 agonistic activity for compound 14 to determine $EC_{50}$=674+1.14 nM. Experiments were performed using the in vitro TLR2 functional bioassay by serially adding (0.001 ng/mL to 10 μg/mL) compound to HEK-293/hTLR2 expressing cells (n=5 assays with 6 wells, R2>0.99). Bar graph B shows the response generated by the TLR2 agonist controls (Pam$_2$CSK4, Pam$_3$CSK4, HKLM) compared to compounds 10 and 14, all at a 1 μg/mL concentration. Graph C is a Dose-response curve for Compound 16 generated by measuring the inhibition of TLR2 agonistic activity of Pam$_2$CSK4 to determine IC$_{50}$=361 nM (R$^2$=0.9436). Experiments were performed using the in vitro TLR2 functional bioassay by serially adding (0.001 ng/mL to 10 μg/mL) compound to HEK-293/hTLR2 expressing cells (n=5 assays with 6 wells, R$^2$>0.99). Graph D shows the significant decrease in agonist response generated by Compound 16 compared to the TLR2 agonist controls (Pam$_2$CSK4, Pam$_3$CSK4, HKLM), all at a 1 ug/mL concentration (p-values <0.00001, n=5).
Figure 4B:
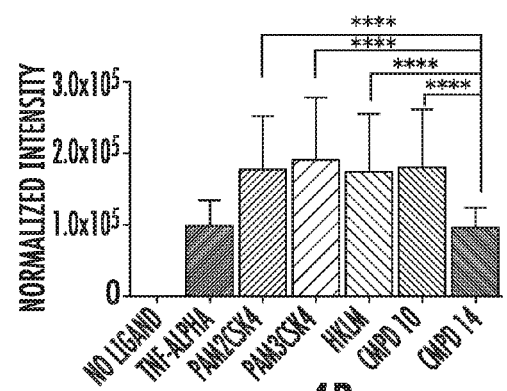
Figure 4C:
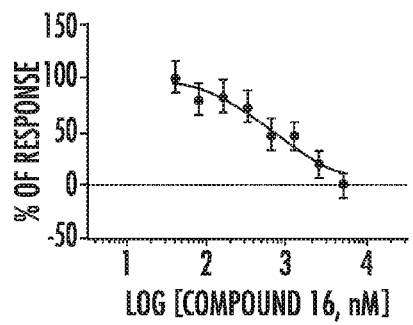
Figure 4D:
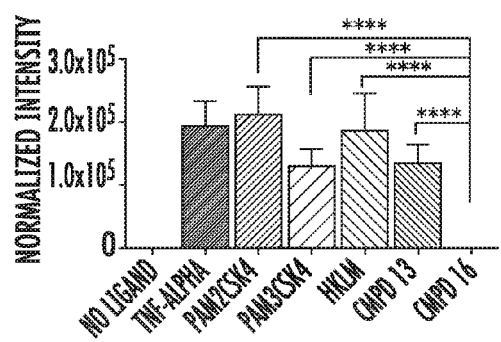

FIG. 3, graph A, shows the saturation binding curve for the HEK293/hTLR2 cells with a $K_d$ of 12±14 nM and $B_{max}$ of 738,713±293,480 AFU ($R^2$=0.7425, n=4 assays×4 replicates). The average number of HEK293/hTLR2 cells per well was 24,700. The saturation binding curve for the SU.86.86 cells determined a $K_d$ of 55±27 nM and $B_{max}$ of 110,534±31,081 AFU ($R^2$=0.9663, n=5 assays×4 replicates) is shown in FIG. 3, graph B. The average number of SU.86.86 cells per well was 33,500. The $B_{max}$ value corresponds to 2.853 fmol and 1.0745 fmol per well for HEK293/hTLR2 and SU.86.86 cells on the linear regression plot of fluorescence versus ligand concentration for compound 11 (y=102862X+4.2741), respectively (FIG. 3, graph C). The amount of TLR2 expressed on the cell surface of the genetically engineered TLR2 expressing cell line, HEK293/hTLR2, was calculated to be 175,000±69,500. The endogenous TLR2 expressing human pancreatic adenocarcinoma cell line, SU.86.86 has 19,300±5428 TLR2 expressed on the cell surface.

In Vitro TLR2 Functional Bioassay

The in vitro TLR2 functional bioassay was developed and optimized for use in high-throughput screening of soluble compound libraries to identify both TLR2 agonists and antagonists. The bioassay measures the induction of NF-κB signaling via TLR2 in HEK-293/hTLR2 cells (Invivogen) and parental HEK-293 cells as a negative control. Cells were seeded at a density of 40,000 per well using a WellMate microplate dispenser (Thermo Fisher Scientific/Matrix) in black 96-well plates with opaque white wells (PerkinElmer, Waltham, Mass.) and then incubated at 37° C. On day 2, the cells were transiently transfected with pNifty-Luc(Invivo-Gen, San Diego, Calif.), an NF-κB inducible reporter plasmid expressing the luciferase reporter gene (Schindler et al., Three NF-kappa B binding sites in the human E-selectin gene required for maximal tumor necrosis factor alpha-induced expression. *Mol Cell Biol* 1994, 14(9):5820-31) using an optimized 4:1 ratio by volume of FugeneHD transfection reagent (Promega, Madison, Wis.) to pNifty-Luc plasmid DNA (1 μg/mL). On day 3, the cells were stimulated with either test peptides or controls adjusted to a final concentration of 1 μg/mL using a NanoDrop spectrophotometer, ND1000 (Thermo Fisher Scientific). Synthetic di- and triacylated LP ligands, Pam$_2$CSK4 and Pam3CSK4 (InvivoGen), were used as positive controls. TNF-α (InvivoGen) was also used as a transfection control that induces NF-κB independently of TLR2. On day 4 after 24 h of peptide stimulation, luciferase induced activity by the induction of NF-κB was measured. The medium was aspirated from the wells using an ELx405 SelectCW plate washer (BioTek, Winooski, Vt.), and 150 μg/mL D-luciferin (Gold Biotechnology, St. Louis, Mo.) was dispensed using the microplate dispensor. The plates were incubated at 37° C. for 5 min. The luminescence intensity was measured using the standard luminescence protocol on a Victor X4 multilabel plate reader equipped with a plate stacker for readout of multiple plates at a time (PerkinElmer, Waltham, Mass.). For each in vitro TLR2 bioassay, at least three different experiments were performed in triplicate (n≥3). Data were analyzed with GraphPad Prism software, and curves were generated with the appropriate nonlinear fit regression analysis.

Compound 14 has an $EC_{50}$ value of 674±1.14 nM cells (n=5 assays with 6 wells, R2>0.99) (FIG. 4, graph A). The monoacyl analog (compound 14) has significantly less agonist potency than its diacyl counterpart (compound 10) and the control ligands (Pam$_2$CSK4) Pam$_3$CSK4, HKLM) (p-values <0.0001, n=5) (FIG. 4, graph B). Conjugation of the near-infrared IR780 fluorescent dye to 14, forming compound 16, resulted in a complete loss in agonist activity. Compound 16 was determined to be a strong TLR2 antagonist ($IC_{50}$=361 nM) using the in vitro TLR2 functional bioassay by serially adding (0.001 ng/mL to 10 μg/mL) compound to HEK-293/hTLR2 expressing cells (n=5 assays with 6 wells, $R^2$=0.9436) (FIG. 4, graph C). FIG. 4, graph D, shows the significant decrease in (complete loss of) agonist activity generated by compound 16 compared to the TLR2 agonist controls (Pam$_2$CSK$_4$, Pam$_3$CSK$_4$, HKLM), all at a 1 μg/mL concentration that inhibits the stimulation of TLR2 NF-κB signaling by Pam$_2$CSK$_4$ (p-values <0.00001, n=5, $R^2$>0.99).

Cytotoxicity Assays

To determine if Compound 16 exhibits in vitro cytotoxicity, cytotoxicity assays were performed according to manufacture instructions using the Dojindo CCK8 Kit. SU.86.86 were treated with Compound 16 for 24 hours over a range of concentrations (40 to 512 ng/mL corresponding to 21 to 2690 nM). Pam$_2$CSK4 was added to SU.86.86 for 24 hours over the same range of concentrations (40 to 512 ng/mL). Three different experiments were performed in triplicate (n≥3). Data were analyzed with GraphPad Prism software.

Figure 5:
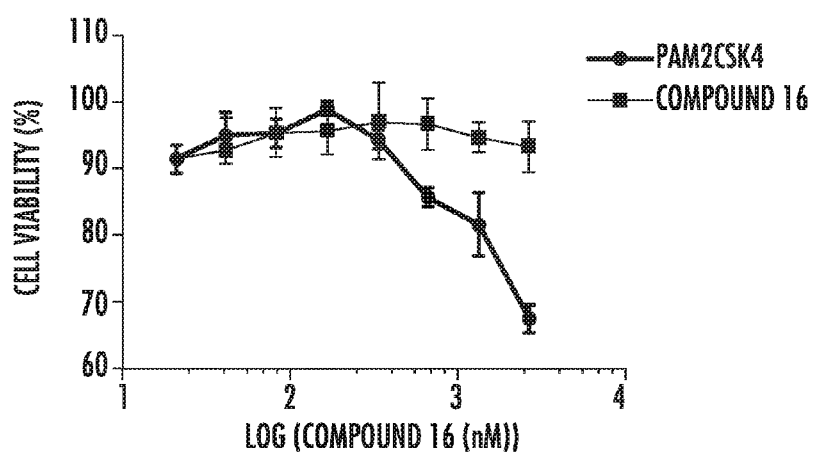
FIG. 5 is a graph showing a comparison of the cytotoxicity of Compound 16 to Pam$_2$CSK4 over a range of concentrations (21 to 2690 nM) in SU.86.86 cells with a significant difference in viability at the higher concentrations from 672 nM to 2690 nM (p-value ≤0.01, n=3 assays).

FIG. 5 shows that Compound 16 has high levels of cell viability at all concentrations tested from 0 to 2.69 μM, while Pam$_2$CSK4 cell viability decreases at higher concentrations past 336 nM. There is a significant difference in the cell viability of cells treated with Compound 16 compared to those treated with Pam$_2$CSK4 at high concentrations for 24 hr (672, 1340 and 2690 nM) (p-value ≤0.01, n=3).

Dose Determination for In Vivo Imaging Studies

Cells (8×10$^6$) were xenografted right (SU.86.86) flanks of female nu/nu mice (Harlan, Indianapolis, Ind.). After 5 weeks, tumors were ready for imaging. A range of dosages from 0.005 to 140 nmol/kg of compound 16 were administered via tail i.v. injection volume of 100 μL. Animals were imaged immediately to check for successful injection. Follow-up imaging was performed 24 h postinjection. Imaging was performed using an IVIS Imaging System, 200 Series (PerkinElmer Xenogen Caliper Life Sciences, Hopkinton, Mass.). Excitation (710-760 nm) and emission (810-875 nm) filters were used in wavelength ranges suitable for in vivo excitation and detection of emitted light of IR780 dye. Acquisition times ranged from 4 to 10 s in order to keep intensity counts above a minimum of 15,000 but below saturation values of ~60,000. Results are displayed in radiant efficiency units in which the fluorescence surface radiance values ((photons/sec/cm$^2$/sr)/μW/cm$^2$) within an image are normalized using a stored reference image that represents the variation in excitation light intensities across the stage, so that images acquired at different times and locations on the stage can be directly compared. Instrument background was determined by removing the animals and repeating the measurements and was subtracted from each image. Autofluorescence was determined by drawing identical ROIs on the instrument background subtracted ICG fluorescence image and corresponding image acquired prior to agent administration, and subtracting the autofluorescence values from the postadministration image.

In Vivo TLR2 Selectivity Experiment

Female athymic nude mice 6-8 weeks old (Harlan) bearing human pancreatic tumor xenografts of SU.86.86 cells on the right flank were used. Mouse weights and tumor volumes were determined using caliper measurements and the formula: volume (mm3)=(length×width$^2$)/2. Images were acquired when the tumors reached an average size of 500 mm$^3$. For the blocked group, a co-injection of 100 nmol/kg of the fluorescently labeled Compound 16 plus 2 μmol/kg Pam$_2$CSK4 (a 20-fold excess) was administered via tail vein injection; for the unblocked group, 100 nmol/kg Compound 16 was administered. Fluorescence images were acquired at time 0 and 24 h using the Caliper Xenogen IVIS200 system (PerkinElmer) with the 710-760 nm excitation and 810-875 nm emission filter set. The fluorescence was quantified using Living Image software, in which the quantified signals were corrected for both instrument and mouse background subtractions. The quantified fluorescence was then plotted using GraphPad Prism software and underwent statistical analysis using Student's t-test.

Figures 6A, 6B:
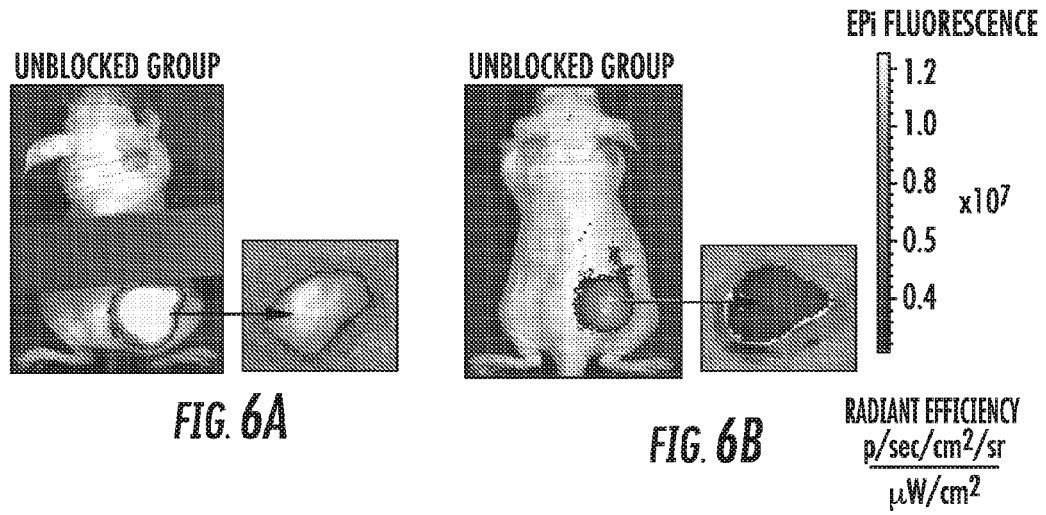
FIG. 6 is a group of images and a graph showing a comparison of representative fluorescence images of nude mice bearing TLR2 expressing human pancreatic tumor xenografts (SU.86.86 cells) acquired at 24 h, where the (image A) unblocked mice were administered 100 nmol/kg Compound 16 and (image B) blocked mice were administered a co-injection of 100 nmol/kg Compound 16 plus 2 μmol/kg Pam$_2$CSK4 (20-fold excess). Ex vivo tumor selectivity was observed in the ex vivo fluorescence images of the unblocked and blocked tumors, and the corresponding IHC staining for TLR2 is also shown. The graph in panel C shows the results in which a significant reduction in the ex vivo fluorescence signal was measured in the blocked tumors compared to the tumors that were not blocked (n=9, p<0.0007), the mean increase in signal (unblocked tumor/blocked tumor) of 16 in the tumor was 2.67 fold.
Figure 6C:
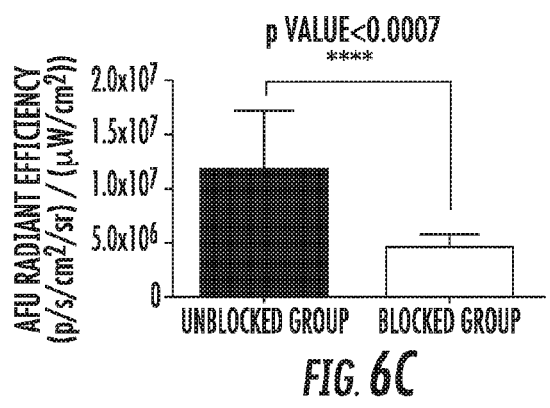
Figure 7A:
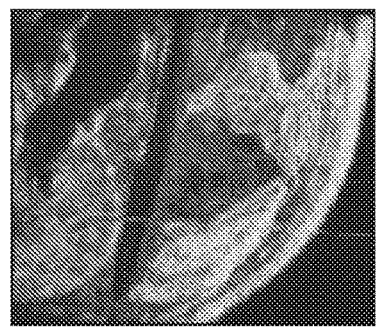
FIG. 7 is a group of images from intraoperative studies. Panel A shows the orthotopic pancreatic tumor xenograft volume was measured prior to surgery in vivo by 3D ultrasound imaging 5 weeks post-injection of SU.86.86 human pancreatic tumor cells. Panel B is an in vivo real-time NIRF image acquired using a clinical imaging platform during fluorescence guided surgical removal of an orthotopic SU.86.86 pancreatic tumor, 24 h post-injection of TLR2Li-780. Panel C is an ex vivo fluorescence image of the same tumor imaged in panel B. Panel D is from in vivo fluorescence tomographic imaging performed pre- and post-survival surgery confirming removal of the tumor.
Figure 7B:
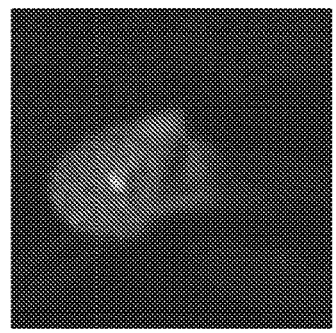
Figure 7C:
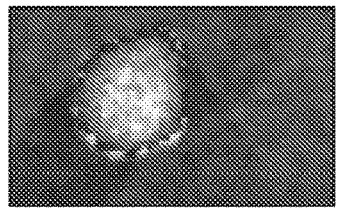
Figure 7D:
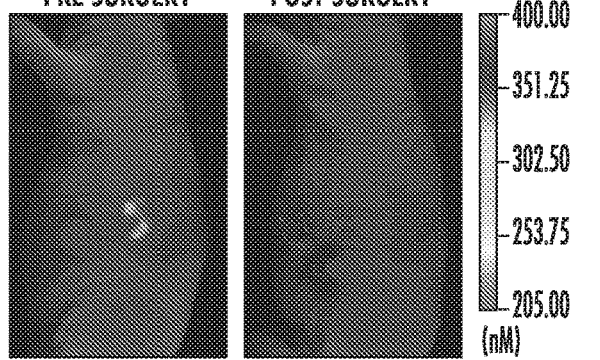

At 24 h post-injection, in vivo fluorescence imaging detected retention of fluorescence signal in the tumor (FIG. 2, graph B). To determine the in vivo selectivity of Compound 16 for TLR2, a blocking study was performed. A significant reduction in the tumor fluorescence was observed 24 h post-injection in the blocked group that received a 20-fold excess of Pam$_2$CSK4 co-injected with 16 compared to the unblocked group receiving only Compound 16 (p<0.0007, n=9) (FIG. 6, images A and B). The mean unblocked tumor fluorescence was 2.67-fold higher than the blocked. Ex vivo imaging confirmed that the fluorescence was associated with the tumors and that the blocked tumors had decreased fluorescence compared to the unblocked tumors (FIG. 7, panels C and D). IHC staining (in progress) confirmed TLR2 expression in the tumors.

Intraoperative Fluorescence Guided Surgery

Prior to surgery, SU.86.86 orthotopic pancreatic tumor xenografts were generated by our published ultrasound-guided injection method and volumes were measured in vivo weekly by 3D ultrasound imaging (FIG. 7, panel A). In vivo fluorescence guided intraoperative surgical removal of orthotopic pancreatic tumors 24 h post-injection of Compound 16 was performed using a clinical real-time imaging platform (FIG. 7, panel B). Ex vivo fluorescence images were acquired that correspond to the in vivo real-time images (FIG. 7, panel C). In vivo tomographic fluorescence imaging was also performed pre- and post-surgery confirming removal of the orthotopic tumor (FIG. 7, Panel D).

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having Formula I-A:

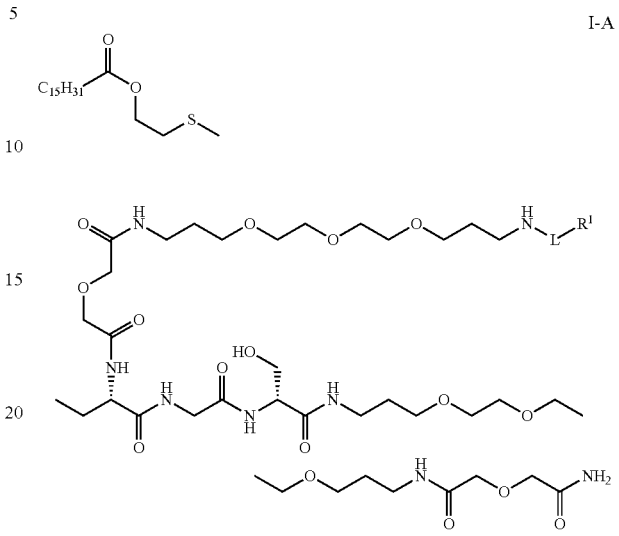

wherein

L is a bond, H, or linker moiety of 1 to 20 atoms; and

R$^1$ is an imaging moiety selected from the group consisting of a UV-Vis moiety, a fluorescent moiety a near-infrared moiety, a luminescent moiety, a phosphorescent moiety, a magnetic spin resonance moiety, a photosensitizing moiety, a photocleavable moiety, a chelating center, a heavy atom, a radioactive isotope, an isotope detectable spin resonance moiety, a paramagnetic moiety, a chromophore, and any combination thereof;

or a pharmaceutically acceptable salt thereof.

2. The compound of claim 1, wherein R$^1$ is the fluorescent moiety.

3. The compound of claim 1, wherein R$^1$ is the radioactive isotope.

4. The compound of claim 1, having the structure

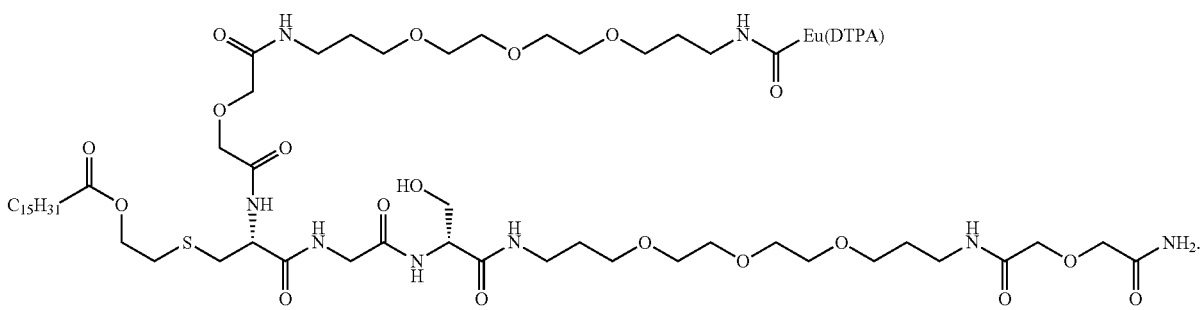

wherein Eu(DPTA) is Europium chelated with diethylenetriaminepentaacetic acid.

5. The compound of claim 1, having the structure

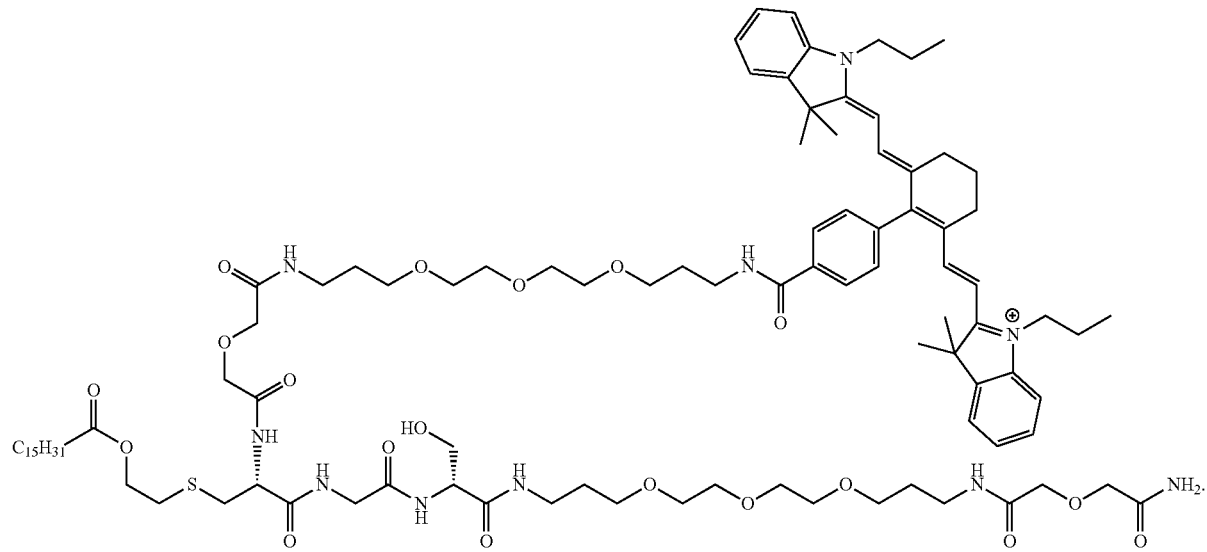

6. A method of treating cancer, comprising administering to a subject a compound of claim 1.

7. The method of claim 6, wherein the cancer is selected from colorectal cancer, ovarian cancer, lung cancer, melanoma, brain cancer, breast cancer, hepatocellular carcinoma, laryngeal cancer, pancreatic adenocarcinoma, stomach cancer, liver cancer, prostate cancer, acute myeloid leukemia, and gastric cancer.

8. The method of claim 7, wherein the cancer is pancreatic cancer.

9. A method of removing a cancer from a region within a subject, comprising administering a compound of claim 1 to the subject, irradiating the region to identify the cancer, and surgically removing the cancer.

10. The method of claim 9, wherein the compound is

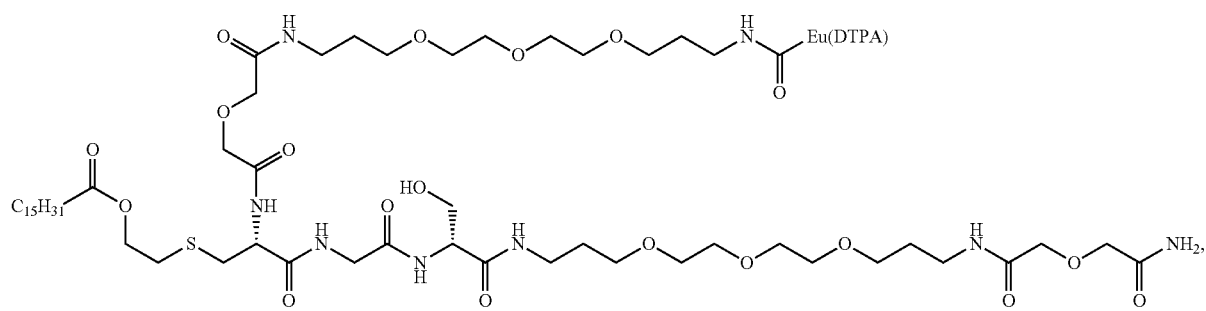

wherein Eu(DPTA) is Europium chelated with diethylenetriaminepentaacetic acid.

11. The method of claim 9, wherein the compound is
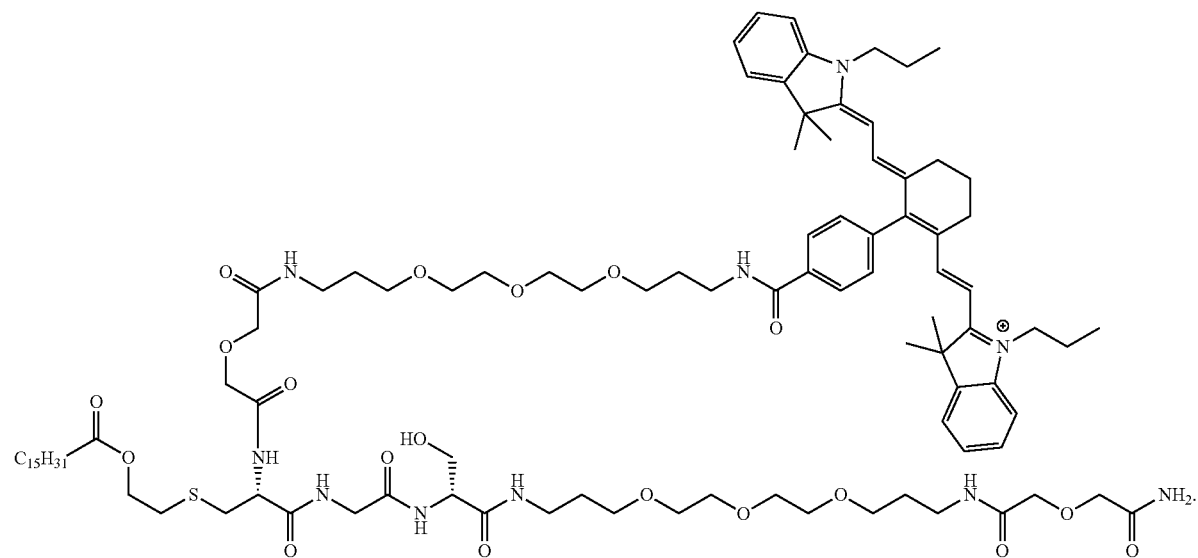
12. A compound having the structure
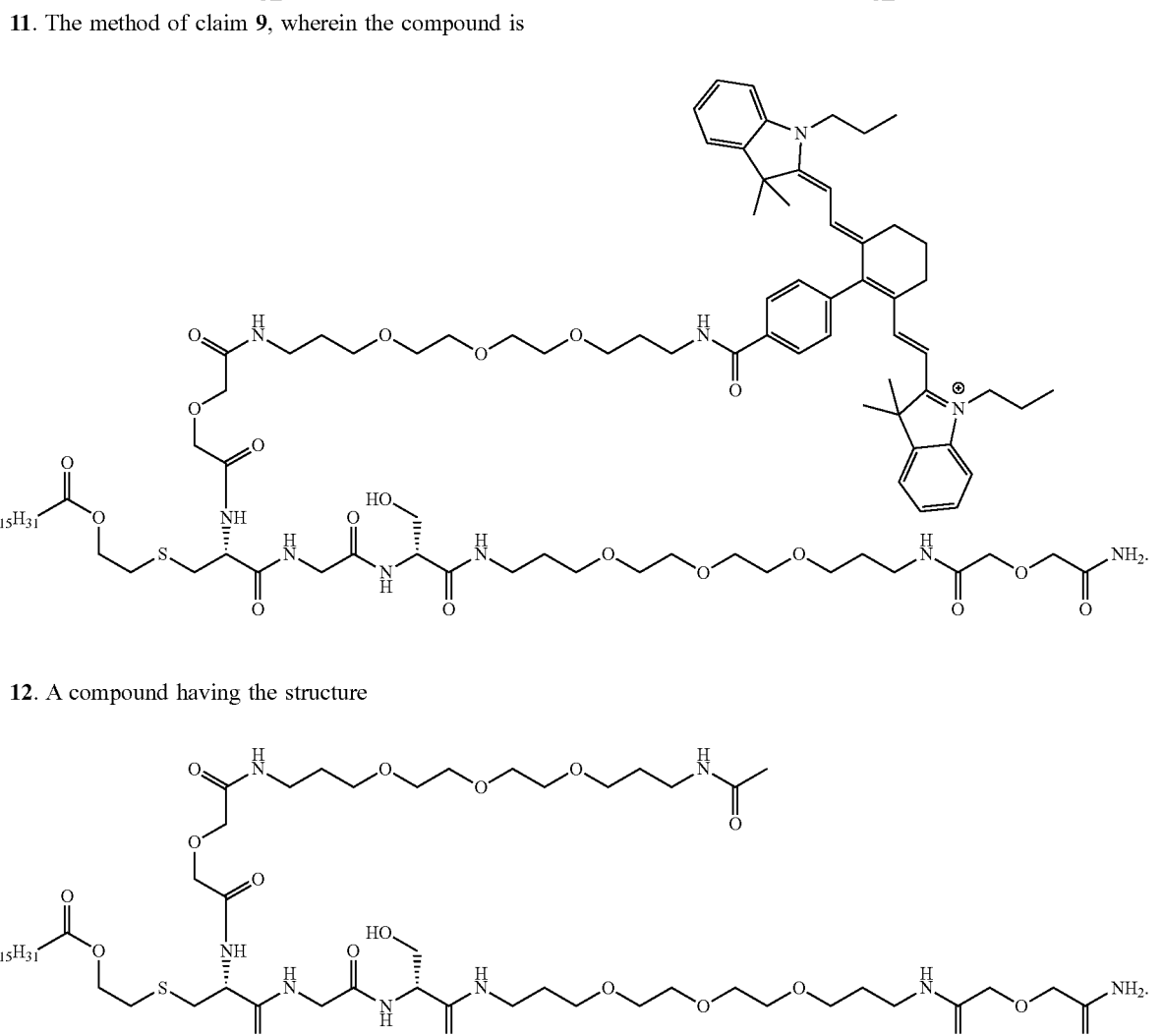
* * * * *